US010016282B2

(12) United States Patent
Seifert et al.

(10) Patent No.: US 10,016,282 B2
(45) Date of Patent: Jul. 10, 2018

(54) INTERVERTEBRAL SPACER AND PLATE

(71) Applicant: GLOBUS MEDICAL, INC., Audubon, PA (US)

(72) Inventors: Jody L. Seifert, Birdsboro, PA (US);
Alex Burkhardt, Leola, PA (US);
Kevin Gahman, Douglasville, PA (US);
Chad Glerum, Pennsburg, PA (US);
Mark Weiman, Coatesville, PA (US);
John Matthews, Philadelphia, PA (US);
Michael Ashleigh, Chester Springs, PA (US); Sean Gill, Boothwyn, PA (US);
Mark Miccio, Lynbrook, NY (US)

(73) Assignee: Globus Medical, Inc., Audubon, PA (US)

( * ) Notice: Subject to any disclaimer, the term of this patent is extended or adjusted under 35 U.S.C. 154(b) by 135 days.

(21) Appl. No.: 14/802,229

(22) Filed: Jul. 17, 2015

(65) Prior Publication Data

US 2017/0014239 A1    Jan. 19, 2017

(51) Int. Cl.
*A61F 2/44* (2006.01)
*A61F 2/30* (2006.01)

(52) U.S. Cl.
CPC .... *A61F 2/447* (2013.01); *A61F 2002/30433* (2013.01); *A61F 2002/30579* (2013.01)

(58) Field of Classification Search
CPC ....... A61F 2/442; A61F 2/4455; A61F 2/4465
USPC ..................... 606/246–249; 623/17.11–17.16
See application file for complete search history.

(56) References Cited

U.S. PATENT DOCUMENTS

| | | | |
|---|---|---|---|
| 6,176,882 B1 | 1/2001 | Biedermann et al. | |
| 6,235,059 B1 | 5/2001 | Benezech et al. | |
| 7,828,849 B2 | 11/2010 | Lim | |
| 7,850,733 B2 | 12/2010 | Baynham et al. | |
| 7,883,543 B2 | 2/2011 | Sweeney | |
| 7,887,595 B1 | 2/2011 | Pimenta | |
| 8,062,375 B2 | 11/2011 | Glerum et al. | |
| 8,105,382 B2 | 1/2012 | Olmos et al. | |
| 8,128,701 B2 | 3/2012 | Kast | |
| 8,157,865 B2 | 4/2012 | Hochschuler et al. | |
| 8,273,129 B2* | 9/2012 | Baynham ................ | A61F 2/447 623/17.16 |
| 8,382,842 B2 | 2/2013 | Greenhalgh et al. | |
| 8,398,713 B2 | 3/2013 | Weiman | |
| 8,480,739 B2 | 7/2013 | Lim et al. | |
| 8,579,981 B2 | 11/2013 | Lim et al. | |
| 8,636,746 B2 | 1/2014 | Jimenez et al. | |
| 8,795,366 B2 | 8/2014 | Varela | |
| 8,864,832 B2 | 10/2014 | Carls et al. | |
| 8,894,711 B2 | 11/2014 | Varela | |
| 8,894,712 B2 | 11/2014 | Varela | |
| 8,932,302 B2 | 1/2015 | Jimenez et al. | |
| 8,986,389 B2 | 3/2015 | Lim et al. | |
| 2008/0306557 A1 | 12/2008 | Altarac et al. | |
| 2011/0319997 A1 | 12/2011 | Glerum et al. | |
| 2011/0319998 A1 | 12/2011 | O'Neil et al. | |
| 2012/0029635 A1 | 2/2012 | Schoenhoeffer et al. | |

(Continued)

*Primary Examiner* — Ellen C Hammond
*Assistant Examiner* — Christina Negrellirodrigue

(57) ABSTRACT

Embodiments herein are generally directed to spinal implants, systems, apparatuses, and components thereof that can be used in spinal fusion and/or stabilization procedures, as well as methods of installation. The spinal implants may include an intervertebral spacer and a plate member.

11 Claims, 15 Drawing Sheets

(56) References Cited

U.S. PATENT DOCUMENTS

| | | |
|---|---|---|
| 2012/0035729 A1 | 2/2012 | Glerum et al. |
| 2012/0330421 A1 | 12/2012 | Weiman |
| 2012/0330422 A1 | 12/2012 | Weiman |
| 2013/0023994 A1 | 1/2013 | Glerum |
| 2014/0012380 A1 | 1/2014 | Laurence et al. |
| 2014/0163682 A1 | 6/2014 | Iott et al. |
| 2014/0163683 A1 | 6/2014 | Seifert et al. |
| 2014/0172103 A1 | 6/2014 | O'Neil et al. |
| 2014/0249628 A1 | 9/2014 | Weiman |
| 2014/0277456 A1* | 9/2014 | Kirschman ............ A61F 2/4455 623/17.11 |
| 2014/0277473 A1* | 9/2014 | Perrow ................... A61F 2/447 623/17.15 |
| 2014/0277487 A1 | 9/2014 | Davenport et al. |
| 2014/0364917 A1 | 12/2014 | Sandstrom et al. |
| 2015/0012097 A1 | 1/2015 | Ibarra et al. |
| 2015/0100129 A1 | 4/2015 | Waugh et al. |
| 2015/0272746 A1 | 10/2015 | Jimenez et al. |
| 2015/0351925 A1 | 12/2015 | Emerick et al. |

* cited by examiner

INTERVERTEBRAL SPACER AND PLATE

FIELD OF THE INVENTION

The present disclosure relates to intervertebral devices and methods used to install these devices.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. One example of a spinal irregularity that may result from disc degeneration is spinal stenosis, the narrowing of a spinal canal, which can result in the compression of spinal nerves such as the spinal cord or cauda equina. In turn, the nerve compression can result in pain, numbness, or weakness. Other examples of conditions that can result from disc degeneration are osteoarthritis and disc herniation.

Often, these irregularities can be treated by performing a discectomy and/or immobilizing a portion of the spine. For example, treatment can include a surgical procedure that involves removal and replacement of an affected intervertebral disc with a prosthesis and the subsequent fusion of adjacent vertebrae. The prosthesis, such as an interbody cage or spacer, may be used either alone or in combination with one or more additional devices such as rods, screws, and/or plates.

SUMMARY OF THE INVENTION

Some embodiments herein are directed a vertebral fusion device that can include a spacer member comprising a first mating element; and a fixation member comprising a first bore extending therethrough and a second mating element, the second mating element configured to articulably engage the first mating element.

Other embodiments herein are directed to a vertebral fusion device that can include a first endplate comprising a first extension portion, the first extension portion comprising a first bore extending therethrough; a second endplate comprising a second extension portion, the second extension portion comprising a second bore extending therethrough; a first ramp configured to mate with the first and second endplates; a second ramp configured to mate with the first and second endplates; wherein the first and second bores each comprise an axis wherein at least one of the axes intersects a vertical, longitudinal plane of the device; and wherein the vertebral fusion device comprises an adjustable height.

Yet other embodiments herein are directed to a vertebral fusion device that can include a first endplate comprising a first extension portion, the first extension portion comprising a first bore extending therethrough; a second endplate comprising a second extension portion, the second extension portion comprising a second bore extending therethrough; a first ramp configured to mate with the first and second endplates; a second ramp configured to mate with the first and second endplates; wherein the first and second bores each comprise an axis wherein at least one of the axes intersects a vertical, longitudinal plane of the device.

Some embodiments herein are directed to a method of installing a vertebral fusion device that can include providing a vertebral fusion device in a collapsed configuration, comprising: a first endplate comprising a first extension portion and a second endplate comprising a second extension portion, both the first and second endplates extending from a first side of the device to a second side of the device; and a first ramp and a second ramp, both the first ramp and the second ramp being configured to mate with the first and second endplates, and both the first ramp and the second ramp extending from the first side of the device to the second side of the device, wherein at least one of the first and second sides of the device is configured to pivotably expand about a pivot point; wherein the device defines a first angle with respect to the pivot point. The method can also include transitioning the fusion device from the collapsed configuration to an expanded configuration, comprising: pivotably expanding at least one of the first and second sides of the device about the pivot point until the device defines a second angle with respect to the pivot point, wherein the second angle is greater than the first angle; and inserting a first fastener into a bore in the first extension portion and inserting a second fastener into a bore in the second extension portion.

Other embodiments herein are directed to a method of installing a vertebral fusion device that can include providing a vertebral fusion device in a collapsed configuration, comprising: a first endplate comprising a first extension portion and a second endplate comprising a second extension portion, both the first and second endplates extending from a first side of the device to a second side of the device; and a first ramp and a second ramp, both the first ramp and the second ramp being configured to mate with the first and second endplates, and both the first ramp and the second ramp extending from the first side of the device to the second side of the device, wherein at least one of the first and second sides of the device is configured to pivotably expand about a pivot point; wherein the device defines a first angle with respect to the pivot point. The method can also include transitioning the fusion device from the collapsed configuration to an expanded configuration, comprising: pivotably expanding at least one of the first and second sides of the device about the pivot point until the device defines a second angle with respect to the pivot point, wherein the second angle is greater than the first angle; and inserting a first fastener into the first extension portion along a first axis and inserting a second fastener into the second extension portion along a second axis, wherein at least one of the first and second axes is offset from a vertical, longitudinal plane of the vertebral fusion device.

Still other embodiments herein are directed to a method of installing a vertebral fusion device that can include providing a vertebral fusion device in a collapsed configuration, comprising: a first endplate comprising a first extension portion and a second endplate comprising a second extension portion, both the first and second endplates extending from a first side of the device to a second side of the device; and a first ramp and a second ramp, both the first ramp and the second ramp being configured to mate with the first and second endplates, and both the first ramp and the second ramp extending from the first side of the device to the second side of the device, wherein at least one of the first and second sides of the device is configured to pivotably expand about a pivot point; wherein the device defines a first angle with respect to the pivot point. The method can also include transitioning the fusion device from the collapsed configuration to an expanded configuration, comprising: pivotably expanding at least one of the first and second sides of the device about the pivot point until the device defines a second angle with respect to the pivot point, wherein the second angle is greater than the first angle; adjusting a position of at least one of the first and second extension portions relative to a body portion of at least one of the first and second endplates; and inserting a first fastener into the first extension portion along a first axis and inserting a second fastener into the second extension portion along a second axis, wherein at least one of the first and second axes is offset from a vertical, longitudinal plane of the vertebral fusion device.

Further areas of applicability of the present disclosure will become apparent from the detailed description provided hereinafter. It should be understood that the detailed description and specific examples, while indicating certain embodiments, are intended for purposes of illustration only and are not intended to limit the scope of the disclosure.

BRIEF DESCRIPTION OF THE DRAWINGS

The present disclosure will become more fully understood from the detailed description and the accompanying drawings, wherein:

FIGS. 13B-E illustrate perspective views of one embodiment of a vertebral fusion device described herein.

DETAILED DESCRIPTION

Figure 1A:
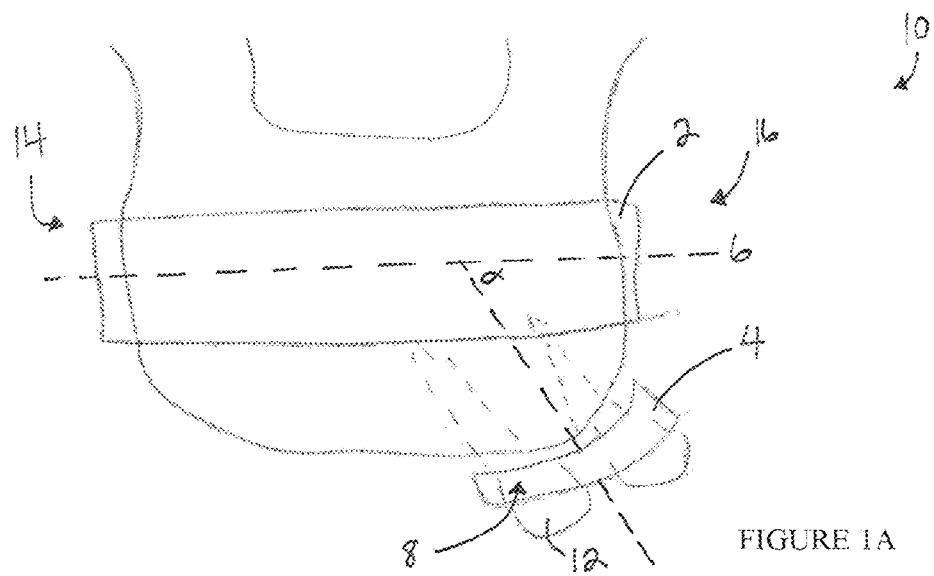
FIG. 1A illustrates a schematic view of one embodiment of a vertebral fusion device described herein.

In a spinal fusion procedure, affected tissue between adjacent vertebrae may be removed and replaced with a prosthesis, such as an interbody cage, spacer, or other spinal implant. A plate and/or screws may also be used to secure the prosthesis within the intervertebral disc space. The intervertebral disc space can be accessed via various approaches (e.g., anterior, posterior, transforaminal, and/or lateral). In a lateral procedure, the prosthesis may be inserted through an incision on a patient's side; advantageously, this type of approach may generally avoid muscles and nerves that may otherwise be encountered in an anterior, posterior, and/or transforaminal approach. However, a lateral approach may be difficult in a patient's lumbar spine (e.g., between the L4 and L5 vertebrae), as the patient's bones, nerves, and/or musculature, such as the iliac crest, lumbar plexus, and/or psoas, can inhibit the trajectory of the screws. Accordingly, disclosed herein are vertebral fusion devices that can include an interbody spacer and a plate configured for use in lateral lumbar interbody fusion (LLIF) procedures, and that can enable implant and screw placement even in the vicinity of the iliac crest and other anatomy.

Some embodiments herein may be directed to vertebral fusion devices that can be configured for insertion between adjacent vertebrae via a lateral procedure (e.g., lateral lumbar interbody fusion). For example, the device may have a length (e.g., as measured between a leading end and a trailing end) that is about 100-300% greater than a width thereof (e.g., as measured in the anterior-posterior direction). The device may also have a length that is configured to laterally span a vertebral endplate. For example, the device may have a length in the range of from about 35 mm to about 65 mm. The device may also have a width in the range of from about 15 mm to about 30 mm. Some embodiments herein may be directed to expandable vertebral fusion devices that can be configured for use in lateral procedures. The expandable vertebral fusion devices described herein may have a variable height and may be configured to collapse to a smaller height prior to insertion and/or expand to a larger height after insertion. In some embodiments, the expanded height can be from about 25% to about 200% greater than the collapsed height. In other embodiments, the expanded height can be from about 100% to about 150% greater than the collapsed height. In some embodiments, the collapsed height can be in the range of from about 5 mm to about 10 mm, and/or the expanded height can be in the range of from about 15 mm to about 20 mm. In some embodiments, the expandable vertebral fusion devices may also have a variable lordotic angle. These devices may include one or more members configured to pivot about a pivot point. These devices may be configured to collapse to a smaller angle (e.g., 10.4°) prior to insertion and/or expand to a larger angle (e.g., 22.5°) after insertion. Accordingly, these devices may be configured for use in minimally-invasive surgery (MIS). For example, they may be inserted through a relatively small incision and/or through a cannula, thereby reducing trauma to the patient. Conversely, the expandable vertebral fusion devices described herein may be configured to expand to a width greater than that of other implants in the art, without requiring a larger incision. Furthermore, the height and/or lordotic angle of the expandable vertebral fusion devices may be adjusted after insertion, thereby providing a customized fit within the intervertebral space.

Components of all of the devices and systems disclosed herein can be made of materials known to those skilled in the art, including metals (e.g., titanium), metal alloys (e.g., stainless steel, titanium alloys, and/or cobalt-chromium alloys), ceramics, polymers (e.g., poly ether ether ketone (PEEK), polyphenylene sulfone (PPSU), polysulfone (PSU), polycarbonate (PC), polyetherimide (PEI), polypropylene (PP), polyacetals, or mixtures or co-polymers thereof), allograft, and/or combinations thereof. For example, a spacer member as described herein may include a polymeric material and a fixation member as described herein may include a metallic material. In some embodiments, the systems and devices may include radiolucent and/or radiopaque materials. In other embodiments, one or more components may be coated with a bone growth-enhancing material, such as hydroxyapatite. The components can also be machined and/or manufactured using techniques known to those skilled in the art. For example, polymeric components may be injection-molded or blow-molded. Additionally, the devices disclosed herein may be used together with materials that encourage bone growth, such as bone graft material, demineralized bone matrix, bone chips, and/or bone morphogenetic proteins. In some embodiments, these materials may advantageously be packed into hollow areas of the devices described herein.

As described herein, the spinal implants of the present disclosure may be configured for placement between two adjacent vertebrae, for example, as part of a spinal fusion procedure. These spinal implants may be referred to as, without limitation, interbody spacers, interbody fusion devices, vertebral fusion devices, interbody cages, and/or intervertebral cages. Each of the spinal implants described herein may include superior and/or inferior surfaces that are configured to engage and/or contact a vertebral endplate or other vertebral surface. In some embodiments, the superior and/or inferior surfaces may be convex, corresponding to the topography of the endplates. Additionally, the superior and/or inferior surfaces of each of the spinal implants described herein may include one or more texturizing members. Examples of such texturizing members include, but are not limited to, projections, bumps, teeth, grooves, peaks, spikes, and/or knurling. These texturizing features may advantageously enhance the interaction or fiction, and/or reduce movement, between the implant and the vertebrae. The spinal implants of the present disclosure may be configured for insertion between adjacent vertebrae. In some embodiments, the spinal implants described herein may be configured for insertion between lumbar vertebrae (e.g., between L4-L5 vertebrae). The spinal implants described herein may be configured for insertion using a minimally-invasive procedure (e.g., through a cannula). The spinal implants described herein may be configured for insertion using a variety of approaches. In some embodiments, the spinal implants may be configured for lateral insertion. In other embodiments, the spinal implants of the present disclosure may be configured for anterior, posterior, and/or transforaminal insertion. Those skilled in the art may appreciate that directional terms such as "anterior," "posterior," "superior," "inferior," "top," and "bottom," and the like may be used herein for descriptive purposes and do not limit the orientation(s) in which the devices may be used. For example, those skilled in the art may appreciate that, in use, a "superior" surface may be installed adjacent an inferior vertebra, and vice versa. Accordingly, a feature described as being on top may actually be oriented towards the bottom after installation.

Some embodiments disclosed herein are directed to a vertebral fusion device that can include a spacer member and a fixation member (e.g., plate). The spacer member and the fixation member can be separate, or they can be integrated. In some embodiments, the device can include two or more fixation members and/or a multi-piece fixation member. In some embodiments, the fixation member(s) may be configured to move relative to the spacer member along one or more paths. The fixation member can include a bore configured to receive a fastener (e.g., bone screw, anchor, and/or staple) therethrough. These embodiments can advantageously direct the trajectory of a fastener, and/or can enable a user to alter the trajectory of a fastener, so as to avoid anatomical structures such as the lumbar plexus, psoas major, and/or iliac crest. In some embodiments, the spacer member can be expandable. For example, the spacer member can include a variable height and/or a variable lordotic angle.

Figure 1B:
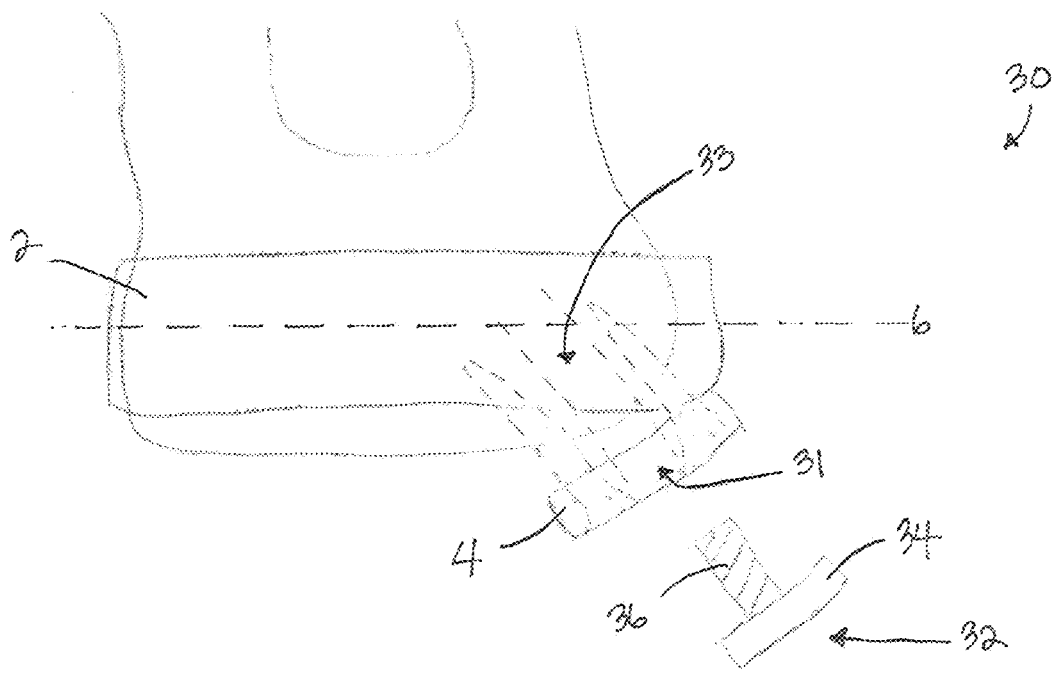
FIG. 1B illustrates a schematic view of one embodiment of a vertebral fusion device described herein.

Turning now to FIGS. 1A-B, some embodiments herein are directed to a vertebral fusion device that can include a spacer member and a fixation member. With respect to FIG. 1A, vertebral fusion device 10 can include a spacer member 2 and a fixation member 4, wherein the fixation member 4 may be configured to be offset from a vertical, longitudinal plane 6 of the spacer member 2. The spacer member 2 may be configured for insertion between adjacent vertebrae via a lateral procedure (e.g., lateral lumbar interbody fusion). For example, the spacer member 2 may have a length (e.g., as measured between a leading end 14 and a trailing end 16) that is about 100-300% greater than a width thereof (e.g., as measured in the anterior-posterior direction). The spacer member 2 may also have a length that is configured to laterally span a vertebral endplate. For example, the spacer member 2 may have a length in the range of from about 40 mm to about 60 mm. The fixation member 4 may include at least one bore 8 configured to receive a fastener 12 therethrough. The fastener 12 may be, for example, a bone screw, anchor, staple, or spike. In some embodiments, the fixation member 4 may include two, three, four, or more bores configured to receive a fastener therethrough. In some embodiments, at least two bores may be horizontally and/or vertically displaced from each other. The fixation member 4 may have a height that is greater than a height of the spacer member 2. For example, the fixation member 4 may have a height that is greater than a distance between two adjacent vertebrae. In some embodiments that include two bores, the two bores may be spaced apart by a distance that is greater than a distance between two adjacent vertebrae. The fixation member 4 may be configured to be offset (e.g., anteriorly) from the vertical, longitudinal plane 6 by an angle $\alpha$, for example, in the range of from about 5° to about 90°. In some embodiments, $\alpha$ may be in the range of from about 5° to about 45°. In other embodiments, $\alpha$ may be in the range of from about 20° to about 30°.

Other embodiments herein are directed to methods of installing the vertebral fusion device 10. In these embodiments, the spacer member 2 may be inserted along a first trajectory (e.g., laterally). The first trajectory may be along and/or parallel to the vertical, longitudinal plane 6. The fixation member 4 may be inserted along a second trajectory that intersects the first trajectory (e.g., obliquely and/or anterolaterally). The first and second trajectories may intersect to form the angle $\alpha$, for example, in the range of from about 5° to about 90°. Fastener 12 may be inserted into bore 8 along a third trajectory that intersects the first trajectory (e.g., obliquely and/or anterolaterally). In some embodiments, the third trajectory may be parallel to the second trajectory.

An alternative embodiment is illustrated in FIG. 1B. As illustrated therein, vertebral fusion device 30 may include some or all of the features of vertebral fusion device 10, unless expressly described otherwise. Additionally, vertebral fusion device 30 may include a securing member 32. The securing member 32 may include a head 34 and an elongate body 36. The head 34 may be configured to engage a tool such as an inserter and/or a driver. The elongate body 36 may include an engagement feature such as threading or ratcheting. For example, in some embodiments the securing member 32 may be a screw. The securing member 32 may be configured to couple the spacer member 2 and/or the fixation member 4. For example, the elongate body 36 may be configured to engage a threaded opening 31 in the fixation member 4 and/or a threaded opening 33 in the spacer member 2. In use, after the spacer member 2, the fixation member 4, and/or the fastener 12 are inserted, the fixation member 4 may be coupled with the spacer member 2. In some embodiments, this step can include coupling the securing member 32 with the fixation member 4 and the spacer member 2, for example, by threading the securing member 32 therein. The securing member 32 may also be inserted along a trajectory (e.g., a fourth trajectory) that is offset from the vertical, longitudinal plane 6. The fourth trajectory may be parallel to the second and/or third trajectories, as described herein with respect to vertebral fusion device 10.

Figure 2A:
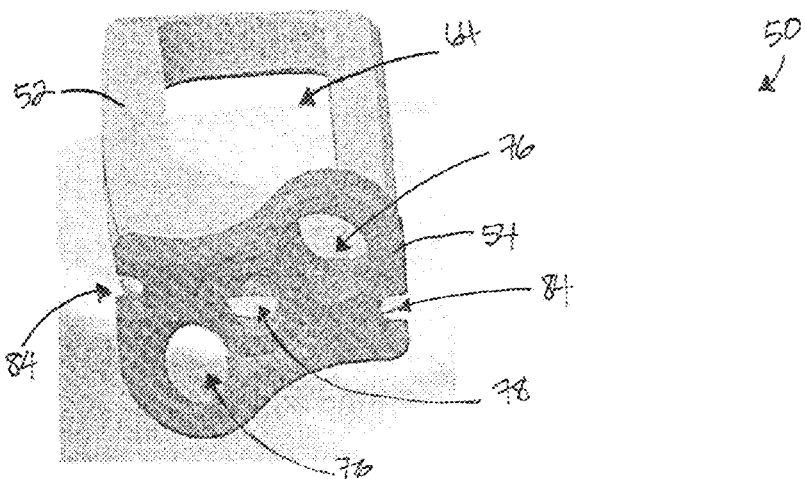
FIGS. 2A-C illustrate perspective views of one embodiment of a vertebral fusion device described herein.
Figure 2B:
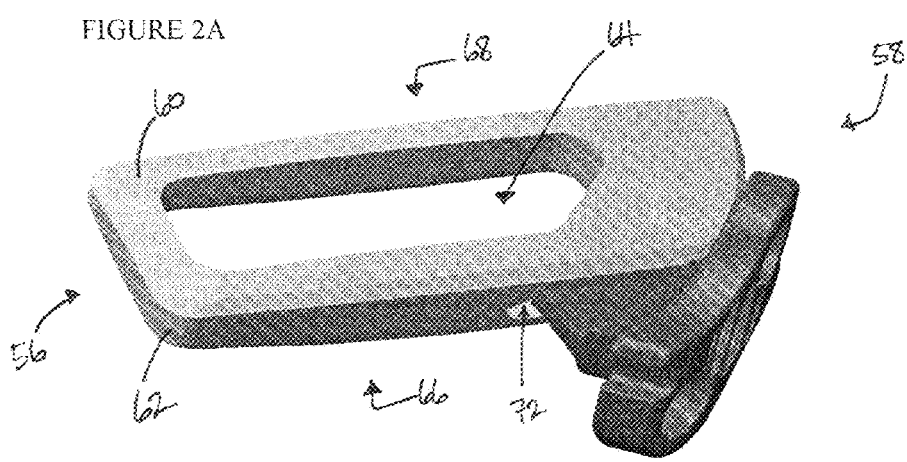
Figure 2C:
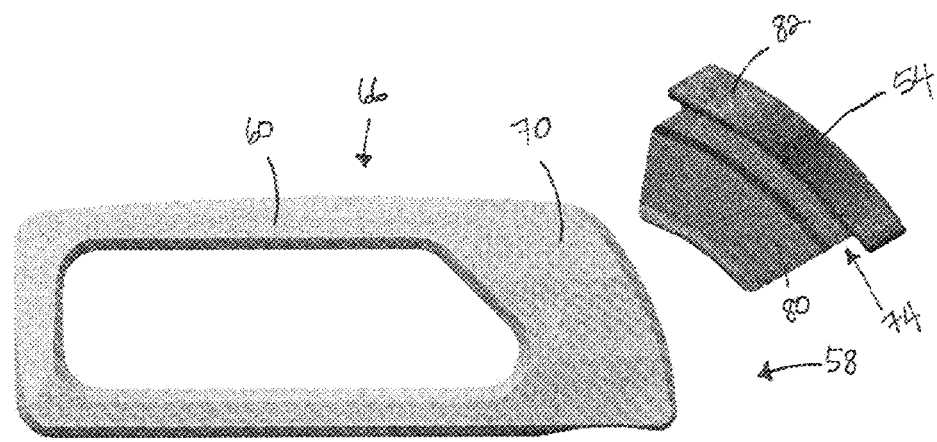

Some embodiments herein are directed to a vertebral fusion device that can include a spacer member and a fixation member, wherein the fixation member is configured to move relative to the spacer member when it is coupled thereto. Turning to FIGS. 2A-C, some embodiments herein are directed to a vertebral fusion device 50 that can include a spacer member 52 and a fixation member 54. As illustrated in FIG. 2B, the spacer 52 can include a first (e.g., leading) end 56, a second (e.g., trailing) end 58, a first (e.g., anterior) side 66, and a second (e.g., posterior) side 68. The spacer member 52 may include an upper (e.g., superior) surface 60, a lower (e.g., inferior) surface (not shown), and an outer side surface 62 along an outer perimeter thereof. The spacer member 52 may be generally rectangular. In some embodiments, the outer side surface 62 can include at least one curved portion 70, as illustrated, for example, in FIG. 2C. The curved portion 70 may appear curved (e.g., concave) when viewed from the upper surface 60 and/or the lower surface. The curved portion 70 may be located at the trailing end 58 and/or anterior side 66 of the spacer member 52. As illustrated in FIGS. 2A-C, the curved portion may extend at least partially along the trailing end 58 and/or anterior side 66. As illustrated in FIGS. 2A-B, the spacer member 52 can include a central cavity 64. In some embodiments, the central cavity 64 may be configured to receive bone growth material therein. The spacer member 52 may be configured for insertion between adjacent vertebrae via a lateral procedure (e.g., lateral lumbar interbody fusion). For example, the spacer member 52 may have a length (e.g., as measured between the leading end 56 and the trailing end 58) that is about 100-300% greater than a width thereof (e.g., as measured in the anterior-posterior direction). The spacer member 52 may also have a length that is configured to laterally span a vertebral endplate. For example, the spacer member 52 may have a length in the range of from about 40 mm to about 60 mm.

In some embodiments, the spacer member 52 can include a first mating element 72, as illustrated in FIG. 2B. As illustrated in FIG. 2B, the first mating element 72 can include a groove, slot, notch, channel, and/or recess. In some embodiments, the groove, slot, notch, channel, and/or recess may include a tapered cross-section. In other embodiments, it may include a T-shaped cross-section, and may be referred to as a T-slot. In yet other embodiments, the first mating element 72 can include a protrusion, projection, lip, and/or overhang. The protrusion and/or projection can also include a tapered cross-section. The first mating element 72 can extend along a curved path. The first mating element may be disposed on the curved portion 70 of the outer side surface 62. In some embodiments, the first mating element 72 may be disposed on at least a portion of the trailing end 58 and at least a portion of the anterior side 66.

The fixation member 54 can include a second mating element 74. As illustrated in FIG. 2C, the second mating element 74 can be disposed on a coupling portion 80 of the fixation member. The coupling portion 80 may be configured to be at least partially disposed between the upper and lower surfaces of the spacer member 52. The coupling portion 80 may be generally perpendicular to a fixation portion 82 of the fixation member 54. In some embodiments, the second mating element 74 can include a groove, slot, notch, channel, and/or recess. The groove, slot, notch, channel, and/or recess may include a tapered cross-section. In other embodiments, it may include a T-shaped cross-section, and may be referred to as a T-slot. In yet other embodiments, the second mating element 74 can include a protrusion, projection, lip, and/or overhang. The protrusion and/or projection can also include a tapered cross-section. The first and/or second mating elements 72, 74 may each extend along a curved path. In some embodiments, the first and second mating elements 72, 74 may include the same radius of curvature.

In some embodiments, the first mating element 72 can include a groove and the second mating element 74 can include a protrusion, or vice versa. Those skilled in the art may appreciate that when the first and second mating elements 72, 74 are engaged, they may form a joint (e.g., a dovetail joint, a tongue and groove joint, and/or a splice joint). Accordingly, the fixation member 54 may be configured to jointedly couple to the spacer member 52. The second mating element 74 may be configured to articulably, pivotably, and/or slideably engage the first mating element 72. The second mating element 74 may be disposed on a leading side of the fixation member 54. For example, the fixation member 54 may be configured to articulate at least partially about the spacer member 52 by translating the second mating element 74 along the first mating element 72.

The fixation member 54 may include at least one bore 76, as illustrated in FIG. 2A. The bore 76 may be disposed on the fixation portion 82 of the fixation member 54. The bore 76 may be configured to receive a fastener therethrough. The fastener may be, for example, a bone screw, anchor, staple, or spike. In some embodiments, the fixation member 54 may include two, three, four, or more bores configured to receive a fastener therethrough. In some embodiments, at least two bores may be horizontally and/or vertically offset from each other. As illustrated in FIG. 2A, the fastener member 54 can include two bores 76 that are horizontally and vertically offset from each other. The fixation member 54 may be configured to extend beyond the upper surface 60 and/or the lower surface of the spacer member 52. In some embodiments, at least one bore 76 may be located above the upper surface 60 of the spacer member 52 when the spacer member 52 and the fixation member 54 are articulably coupled. The fixation member 54 may have a height that is greater than a height of the spacer member 52 (e.g., as measured between the upper surface 60 and the lower surface). For example, the fixation member 4 may have a height that is greater than a distance between two adjacent vertebrae. In some embodiments that include two bores, the two bores may be spaced apart by a distance that is greater than a distance between two adjacent vertebrae. The fixation member 54 can also include a receptacle 78 therethrough. The receptacle 78 can include a threaded interior. In some embodiments, the receptacle 78 can be configured to threadably receive an inserter or implant holder therein. The fixation portion 82 of the fixation member 54 can also include one or more notches 84, as illustrated in FIG. 2A. The notches 84 may each be configured to engage a protrusion, such as a tab, on the inserter. In use, the protrusion may key into the notch 84 and/or the spacer member 52, advantageously inhibiting motion of the fixation member 54 during insertion.

In some embodiments, the vertebral fusion device 50 can also include a locking member (not shown). The locking member can be configured to reversibly engage the spacer member 52 and/or the fixation member 54. In some embodiments, the locking member can include a clamp, clasp, and/or catch. The locking member can be configured to inhibit movement of the fixation member 54 relative to the spacer member 52 when in a locked configuration. When in an unlocked configuration, the locking member can allow movement of the fixation member 54 relative to the spacer member 52. The vertebral fusion device 50 can reversibly transition between the locked and unlocked configuration.

Also described herein are methods for installing the vertebral fusion device 50. These methods can include providing the vertebral fusion device 50, wherein the spacer member 52 and the fixation member 54 are articulably, pivotably, and/or slideably engaged (e.g., the first and second mating elements 72, 74 may be articulably, pivotably, and/or slideably engaged). In embodiments that include a locking member, the vertebral fusion device 50 may be provided in the locked configuration as described herein. In some embodiments, the vertebral fusion device 50 may be provided (e.g., inserted) between two adjacent vertebrae (e.g., between the L4 and L5 vertebrae), for example, along a lateral approach. In some embodiments, an inserter may be coupled to the vertebral fusion device 50 during the insertion process, for example, by threadably engaging the receptacle 78 and/or keying into the notches 84. In some embodiments, the inserter may be coupled to both the fixation member 54 and the spacer member 52. Advantageously, the inserter may inhibit movement of the fixation member 54 during insertion and/or placement. In embodiments that include a locking member, the device 50 may then be unlocked, e.g., by releasing the locking member. A position (e.g., orientation) of the fixation member 54 (e.g., the position of bore 76) may then be adjusted relative to the spacer member 52. The position of the fixation member 54 may be adjusted, for example, by articulating, pivoting, and/or sliding the fixation member 54 along the path defined by the first mating element 72. The method can also include inserting a first fastener member into the bore 76. In some embodiments, the first fastener member may be inserted along an anterolateral trajectory. In other embodiments, the first fastener member may be inserted along an upwards trajectory (e.g., towards a superior vertebra). In use, those skilled in the art may appreciate that the vertebral fusion device 50 may advantageously enable a user to adjust the position of the bore 76, thereby adjusting fastener placement. Accordingly, a user may be able to position the bore 76 to avoid certain anatomical structures such as the psoas major, lumbar plexus, and/or iliac crest.

Figure 2D:
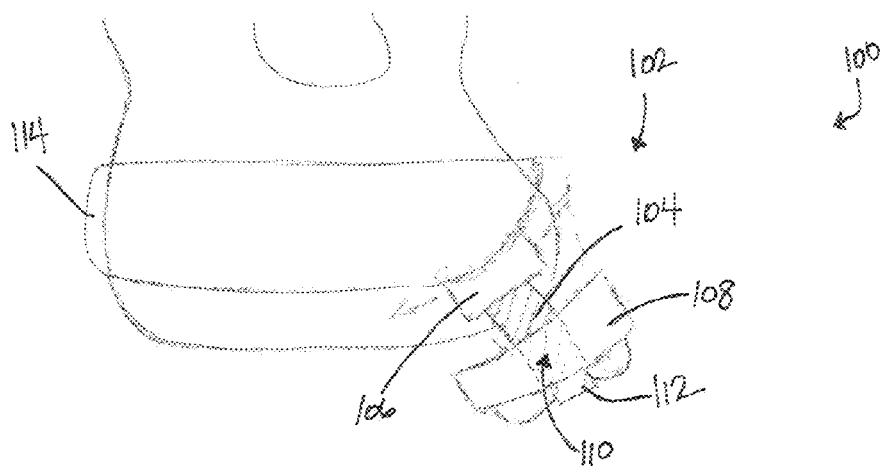
FIG. 2D illustrates a schematic view of one embodiment of a vertebral fusion device described herein.

An alternative embodiment, vertebral fusion device 100, is illustrated in FIG. 2D. Unless expressly described otherwise, vertebral fusion device 100 may include some or all of the features of vertebral fusion device 50. For example, vertebral fusion device 100 may include a spacer member 114 which includes some or all of the same features as spacer member 52. Vertebral fusion device 100 can include a modified fixation member 102. The fixation member 102 can include a threaded post 104, a coupling portion 106, and a fixation portion 108. The fixation portion 108 can include one or more bores (not shown) as described with respect to fixation member 54. The coupling portion 106 can include some or all of the features of coupling portion 80 (e.g., a mating element as described herein). The threaded post 104 can extend, e.g., proximally, from the coupling portion 106. The fixation portion 108 can include a through-hole 110 configured to receive at least a portion of the threaded post 104 therethrough. The through-hole 110 may include a smooth (e.g., non-threaded) interior surface. The fixation portion 108 may be coupled to an actuator 112. The actuator 112 may include a threaded hole configured to mate with the threaded post 104. The actuator 112 can also include an exterior tool-engaging surface. In some embodiments, the actuator 112 can include a nut. In use, the fixation portion 108 may be configured to translate along an axis defined by the threaded post 104, towards and/or away from the spacer member 114.

Also described herein are methods for installing the vertebral fusion device 100. These methods can be the same or similar to those described with respect to the vertebral fusion device 50. Additionally, the step of adjusting a position (e.g., orientation) of the fixation member 102 can include adjusting (e.g., increasing and/or reducing) a distance between the spacer member 114 and the fixation member 102. The distance can be measured horizontally. The step of adjusting the fixation member 102 can include engaging the actuator 112. In embodiments where the actuator 112 includes a nut, this step can include threading or unthreading the nut along the threaded post 104. As the nut travels along the threaded post 104, it may advantageously also cause translational motion of the fixation member 102 in the same direction (e.g., proximally and/or distally). Advantageously, the ability to adjust the position of the fixation member 102 (e.g., the bore(s)) by translation and articulation can provide increased freedom to a user with regards to fastener placement.

Figure 3A:
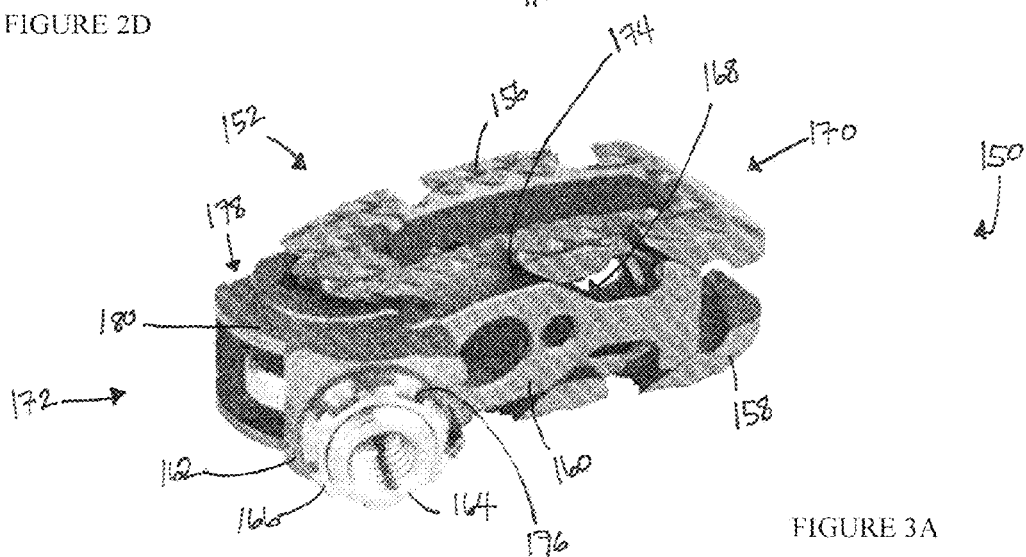
FIG. 3A illustrates a perspective view of one embodiment of a vertebral fusion device described herein.
Figure 3B:
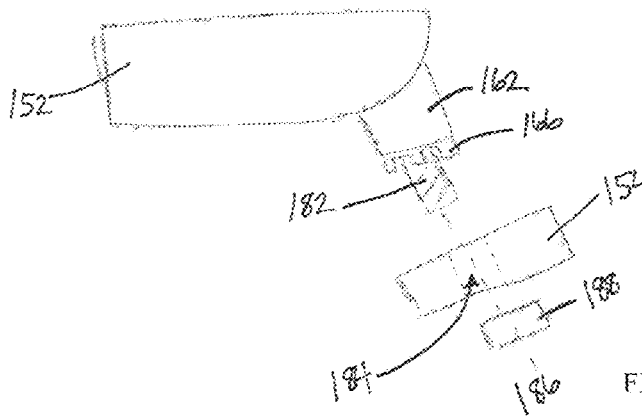
FIG. 3B illustrates a schematic view of one embodiment of a vertebral fusion device described herein.

Other embodiments herein are directed to a vertebral fusion device that can include a movable (e.g., articulable and/or translatable) fixation member as described herein and that can also include an expandable spacer member. The expandable spacer member can include a variable height (e.g., as measured between an upper surface and a lower surface). The expandable spacer member may be generally rectangular, and in some embodiments may be configured for lateral insertion as described herein. Turning to FIGS. 3A-B, vertebral fusion device 150 can include expandable spacer member 152. The expandable spacer member 152 can include a first (e.g., upper) endplate 156, a second (e.g., lower) endplate 158, a frame 160, an articulating screw support 162, a link 164, and a nut 166. The expandable spacer member 152 may also include a drive link (not shown). The drive link may be configured to engage the first and second endplates 156, 158 and may be configured to pull and/or displace the endplates 156, 158 relative to the frame 160. The expandable spacer member 152 may also include a first (e.g., distal and/or leading) end 170 and a second (e.g., proximal and/or trailing) end 172. In some embodiments, vertebral fusion device 150 may include one or more features of the devices described in U.S. Patent Publication No. 2014/0249628, entitled "ARTICULATING EXPANDABLE INTERVERTEBRAL IMPLANT," published on Sep. 4, 2014, which is hereby incorporated by reference herein in its entirety for all purposes.

The frame 160 can include one or more lift ramps 168 on the upper and/or lower surfaces thereof. Each lift ramp 168 may have a surface that is inclined from an intermediate portion of the frame 160 towards the proximal end 172. Each lift ramp 168 may be configured to slideably engage an expansion ramp 174 on the first and/or second endplates 156, 158. Each expansion ramp 174 may have a surface that is inclined from an intermediate portion of the first and/or second endplates 156, 158 towards the distal end 170. In use, the spacer member 152 may be expanded by translating the frame 160 relative to the first and second endplates 156, 158. The lift ramps 168 may engage the expansion ramps 174 and urge the first and second endplates 156, 158 apart, thereby increasing the height of the spacer member 152.

The nut 166 can include internal threads that may be configured to mate with external threads of the link 164. The nut 166 can also include one or more tool-engaging portions 176 disposed on an outer surface thereof. The nut 166 may be rotatably retained along a fixed axial orientation within the articulating screw support 162. In use, a tool (e.g., a driver) may engage and rotate the nut 166. As the nut 166 rotates, link 164 may be advanced or withdrawn with respect to the frame 160, thereby moving endplates 156, 158 with respect to the frame 160 and causing an expansion or contraction of the height of the expandable spacer member 152.

The articulating screw support 162 may be movably (e.g., slideably, articulably, and/or pivotably) coupled to the frame 160. The frame 160 can also include a first mating element 178. The first mating element 178 can include a groove, slot, notch, channel, and/or recess. In some embodiments, the groove, slot, notch, channel, and/or recess may include a tapered cross-section. In other embodiments, it may include a T-shaped cross-section, and may be referred to as a T-slot. In yet other embodiments, the first mating element 178 can include a protrusion, projection, lip, and/or overhang. The protrusion and/or projection can also include a tapered cross-section. The first mating element 178 may be disposed on a curved portion of the trailing end 172. In some embodiments, the first mating element 178 may be disposed on at least a portion of the trailing end 172 and/or at least a portion of an anterior side.

The articulating screw support 162 can include a second mating element 180. The second mating element 180 may be disposed on an inner surface of the articulating screw support 162. In some embodiments, the second mating element 180 can include a groove, slot, notch, channel, and/or recess. The groove, slot, notch, channel, and/or recess may include a tapered cross-section. In other embodiments, it may include a T-shaped cross-section, and may be referred to as a T-slot. In yet other embodiments, the second mating element 180 can include a protrusion, projection, lip, and/or overhang. The protrusion and/or projection can also include a tapered cross-section. The first and/or second mating elements 178, 180 may each extend along a curved path. In some embodiments, the first and second mating elements 178, 180 may include the same radius of curvature.

In some embodiments, the first mating element 178 can include a groove and the second mating element 180 can include a protrusion, or vice versa. Those skilled in the art may appreciate that when the first and second mating elements 178, 180 are engaged, they may form a joint (e.g., a dovetail joint, a tongue and groove joint, and/or a splice joint). Accordingly, the articulating screw support 162 may be configured to jointedly couple to the expandable spacer member 152. The second mating element 180 may be configured to articulably, pivotably, and/or slideably engage the first mating element 178. For example, the articulating screw support 162 may be configured to articulate at least partially about the expandable spacer member 152 by translating the second mating element 180 along the first mating element 178.

In some embodiments, the articulating screw support 162 can be configured to engage a fixation member, such as fixation member 154, illustrated in FIG. 3B, or any other fixation members described herein. The fixation member 154 can be directly or indirectly attached, mounted, and/or coupled to the articulating screw support 162. In some embodiments, the fixation member 154 can be mechanically coupled to the articulating screw support 162. In use, the nut 166 can be movable, thereby enabling expansion and/or contraction of the expandable spacer member 152 from a variety of approaches. Additionally, the fixation member can also be movable, thereby enabling a user to position the fixation member in an orientation that avoids certain anatomical structures as described herein.

As illustrated in FIG. 3B, in some embodiments, the fixation member 154 can be indirectly engaged with the articulating screw support 162. The vertebral fusion device 150 can include a threaded post 182. In some embodiments, the threaded post 182 may be an axial extension of link 164 (e.g., the threaded post 182 may extend lengthwise along axis 186). The fixation member 154 can include some or all of the features of fixation member 102. For example, fixation member 154 can include a through-hole 184 configured to receive at least a portion of the threaded post 182 therethrough. The through-hole 184 may include a smooth (e.g., non-threaded) interior surface. The vertebral fusion device 150 may also include an actuator 188. The actuator 188 may include a threaded hole configured to mate with the threaded post 182. The actuator 188 may also include an exterior tool-engaging surface. In some embodiments, the actuator 188 can include a nut. In use, the fixation member 154 may advantageously be configured to translate along the axis 186, towards and/or away from the expandable spacer member 152.

Also described herein are methods for installing the vertebral fusion device 150. These methods can include providing the vertebral fusion device 150 in a collapsed configuration, wherein the device 150 has a first height (e.g., as measured from an upper surface of endplate 156 to a lower surface of endplate 158). In some embodiments, this step can include inserting the vertebral fusion device between two adjacent vertebrae (e.g., between the L4 and L5 vertebrae), for example, along a lateral, oblique, or anterolateral approach. These methods can also include adjusting a position (e.g., orientation) of the link 164 and/or the fixation member 154 relative to the expandable spacer member 152. The position of the link 164 and/or fixation member 154 can be adjusted, for example, by articulating, pivoting, and/or sliding the articulating screw support 162 along the path defined by the first mating element 178. These methods can also include expanding the vertebral fusion device 150 to an expanded configuration, wherein the device 150 has a second height that is greater than the first height. This step can include rotating the nut 166, thereby applying a force to the frame 160 and separating the endplates 156, 158 as described herein. In some embodiments, this step can also include inserting a tool (e.g., a driver) which engages and rotates the nut 166. The tool can be inserted along a lateral, oblique, or anterolateral approach. Advantageously, a curved path of the first mating element 178 can enable actuation of nut 166 at an angle with respect to a longitudinal axis of spacer member 152. In this manner, spacer member 152 may be inserted into the body along a non-linear path, for example during a transforaminal, posterior, and/or lateral insertion, and articulating screw support 162 may be positioned to be more readily accessible along the insertion path (e.g., oblique and/or anteriolateral) to a tool end which engages nut 166 for rotation, thereby minimizing disturbance of body tissue. In some embodiments, the device 150 can be inserted along a lateral path and the tool can be inserted along an oblique and/or anteriolateral path. In other embodiments, the device 150 can be inserted along an oblique and/or anteriolateral path and articulated into a lateral position (e.g., the expandable spacer member 152 can articulate relative to the link 164 and/or fixation member 154).

The method can also include inserting a first fastener member into a bore on the fixation member 154. In some embodiments, the first fastener member may be inserted along an anteriolateral and/or oblique trajectory. In other embodiments, the first fastener member may be inserted along an upwards trajectory (e.g., towards a superior vertebra). In use, those skilled in the art may appreciate that the vertebral fusion device 150 may advantageously enable a user to adjust the position of the bore, thereby adjusting fastener placement. Accordingly, a user may be able to position the bore to avoid certain anatomical structures such as the psoas major, lumbar plexus, and/or iliac crest.

In some embodiments, for example, those relating to the vertebral fusion device illustrated in FIG. 3B, the step of adjusting a position (e.g., orientation) of the fixation member 154 can include adjusting (e.g., increasing and/or reducing) a distance between the spacer member 152 and the fixation member 154. The distance can be measured along axis 186. The step of adjusting the fixation member 154 can include engaging the actuator 188. In embodiments where the actuator 188 includes a nut, this step can include threading or unthreading the nut along the threaded post 182. As the nut travels along the threaded post 182, it may advantageously also cause translational motion of the fixation member 154 in the same direction (e.g., proximally and/or distally). Advantageously, the ability to adjust the position of the fixation member 154 (e.g., the bore(s)) by translation and articulation can provide increased freedom to a user with regards to fastener placement.

Figure 4:
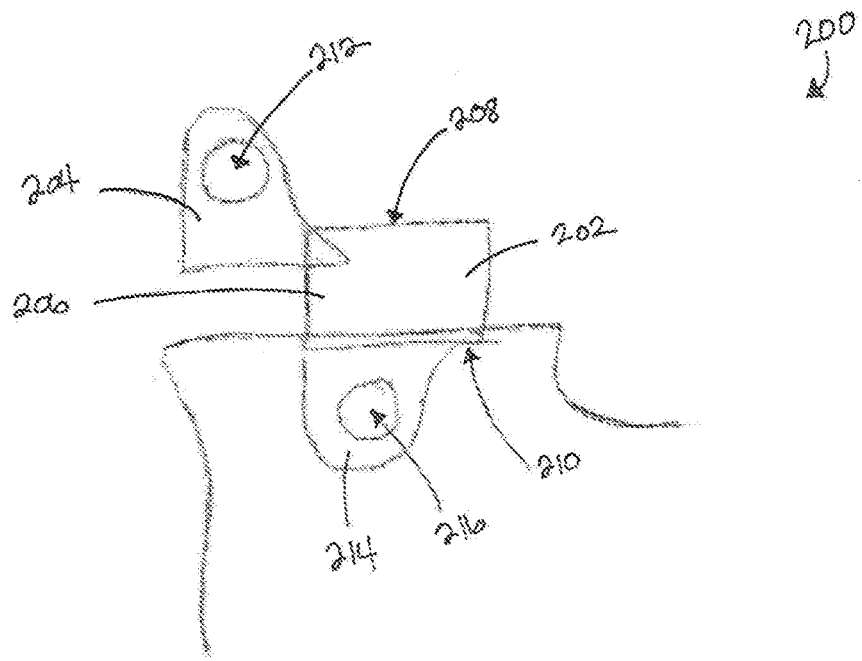
FIG. 4 illustrates a schematic view of one embodiment of a vertebral fusion device described herein.

Turning to FIG. 4, some embodiments herein are directed to a vertebral fusion device 200 that can include a spacer member 202 and a first movable fixation member 204. The first movable fixation member 204 can be configured to be moveably (e.g., articulably, pivotably, and/or slideably) coupled and/or engaged to the spacer member 204, as described herein with respect to, e.g., vertebral fusion devices 50, 100, and/or 150. For example, the first movable fixation member 204 can include a second mating element configured to engage a corresponding first mating element on the spacer member 202. In some embodiments, the first movable fixation member 204 can be configured to translate towards and/or away from the spacer member 202, for example, as described herein with respect to vertebral fusion device 100. The first movable fixation member 204 can include a height that, when coupled to the spacer member 202, extends from a central portion 206 of the spacer member to a position above and/or beyond an upper or lower surface 208, 210 of the spacer member 202. As illustrated in FIG. 4, the height of the first movable fixation member 204 can extend beyond/above the upper surface 208 of the spacer member 202. In these embodiments, the first movable fixation member 204 may be referred to as an upper fixation member. In other embodiments, the height of the first movable fixation member 204 can extend beyond/below the lower surface 210 of the spacer member. In these embodiments, the first movable fixation member 204 may be referred to as a lower fixation member.

As illustrated in FIG. 4, in some embodiments, the first movable fixation member 204 can include a single bore 212. The bore 212 can be configured to receive a fastener (e.g., a bone screw, anchor, and/or staple) therethrough. In other embodiments, the first movable fixation member 204 can include two or more bores. The two or more bores may be horizontally displaced relative to each other (e.g., displaced along a width of the fixation member 204). In some embodiments, the two or more bores may be vertically aligned (e.g., aligned along the height of the fixation member 204).

As illustrated in FIG. 4, the vertebral fusion device 200 can include a second fixation member 214. The second fixation member 214 may be movable or stationary. In embodiments where the second fixation member 214 is movable, it may include some or all of the same features as first fixation member 204. In these embodiments, the spacer member 202 may include an additional mating element (e.g., curved tongue or groove) configured to engage a corresponding mating element on the second fixation member 214. In embodiments where the second fixation member 214 is stationary, it may be coupled (e.g., attached) to the spacer member 202. In some embodiments, the second fixation member 214 and the spacer member 202 can together make up a unitary body. The second fixation member 214 can include a height that, when coupled to the spacer member 202, extends from the central portion 206 of the spacer member 202 to a position above and/or beyond an upper or lower surface 208, 210 of the spacer member 202. As illustrated in FIG. 4, the height of the second fixation member 214 can extend beyond/below the lower surface 210 of the spacer member 202. In these embodiments, the second fixation member may be referred to as the lower fixation member. In other embodiments, the height of the second fixation member 214 can extend beyond/above the upper surface 208 of the spacer member 202. In these embodiments, the second fixation member may be referred to as the upper fixation member. As illustrated in FIG. 4, the second fixation member 214 may extend away from the spacer member 202 in a direction opposite that of the first fixation member 204.

Embodiments herein are also directed to methods of installing the vertebral fusion device 200. These methods can include some or all of the steps described herein with respect to vertebral fusion devices 50, 100, and 150, for example. These methods can include providing the vertebral fusion device 200, wherein the spacer member 202 and the fixation member 204 are articulably, pivotably, and/or slideably engaged (e.g., the first and second mating elements (not shown) may be articulably, pivotably, and/or slideably engaged). In embodiments that include a locking member, the vertebral fusion device 200 may be provided in a locked configuration. The locking member may inhibit movement of the movable fixation member(s). In some embodiments, the vertebral fusion device 200 may be provided (e.g., inserted) between two adjacent vertebrae (e.g., between the L4 and L5 vertebrae), for example, along a lateral approach. In embodiments that include a locking member, the device 200 may then be unlocked, e.g., by releasing the locking member. A position (e.g., orientation) of the first movable fixation member 204 (e.g., the position of bore 212) may then be adjusted relative to the spacer member 202. The position of the first movable fixation member 204 may be adjusted, for example, by articulating, pivoting, and/or sliding the fixation member 204 along the path defined by the first mating element. In some embodiments, this step can also include axially translating the fixation member 204 towards and/or away from the spacer member 202. The method can also include inserting a first fastener member into the bore 212. In some embodiments, the first fastener member may be inserted along an anterolateral trajectory. In other embodiments, the first fastener member may be inserted along an upwards trajectory (e.g., towards a superior vertebra).

In embodiments where the second fixation member 214 is stationary, a second fastener member can be inserted into bore 216 either before or after the first fastener member is inserted into bore 212. Advantageously, the second fixation member 214, when stationary, can provide stability to the device 200 while the first fixation member 204 can provide adjustable fastener placement. In embodiments where the second fixation member 214 is movable, methods herein can also include the steps of adjusting a position (e.g., orientation) of the second fixation member 214 relative to the spacer member 202 and inserting a fastener member into a bore thereof. In these embodiments, the first and second fixation members 204, 214 may advantageously be independently adjustable. Accordingly, each of the first and second fixation members 204, 214 may be positioned differently to accommodate the particular anatomical features of a patient and/or the planned trajectory of the associated fastener (e.g., towards the inferior vertebra or towards the superior vertebra).

Other embodiments herein are directed to vertebral fusion devices that can include a spacer member and a fixation member, wherein the fixation member is configured to translate (e.g., telescope, extend, and/or retract) relative to the spacer member. In some embodiments, the fixation member may be configured to translate along a horizontal axis. In other embodiments, the fixation member may be configured to translate along a vertical axis. In yet other embodiments, the fixation member may be configured to translate along an axis that defines an angle in the range of from about 0° to about 180° relative to a side surface of the spacer member.

Figure 5:
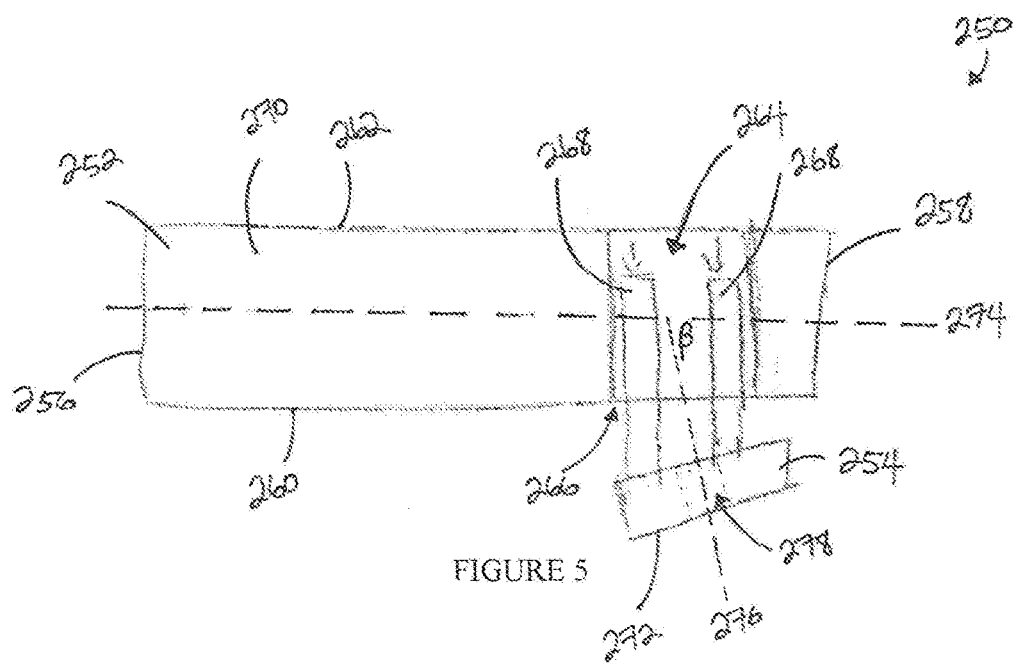
FIG. 5 illustrates a schematic view of one embodiment of a vertebral fusion device described herein.

As illustrated in FIG. 5, vertebral fusion device 250 can include a spacer member 252 and a fixation member 254, wherein the fixation member 254 can be translatably coupled to and/or engaged with the spacer member 252. The spacer member 252 can include a first (e.g, distal and/or leading) side 256, a second (e.g., proximal and/or trailing) side 258, a third (e.g., anterior) side 260, and/or a fourth (e.g., posterior) side 262. The four sides can define a generally rectangular shape. The spacer member 252 can include a vertical, longitudinal plane 274. The spacer member 252 can also include a cavity 264. The cavity 264 can include an opening 266 on the third side 260 of the spacer member 252. The spacer member 252 can also include a first mating element (not shown). The first mating element of the spacer member 252 can be configured to engage the second mating element 268 of the fixation member 254, described herein. In some embodiments, the spacer member 252 can include two or more first mating elements. The first mating element may be disposed within the cavity 264. The first mating element can include, for example, a ramp, rack, and/or track. In some embodiments, the first mating element can define a curved, angled, and/or straight path. The path may extend generally transversely towards and/or away from the opening 266. In some embodiments, the path may be parallel to a horizontal plane of the spacer member 252. In other embodiments, the path may be perpendicular or skewed to the horizontal plane.

The fixation member 254 can include a second mating element 268. The fixation member 254 can include two or more second mating elements 268. The second mating element 268 may be configured to be disposed within the cavity 264 of the spacer member 252. The second mating element 268 can include, for example, a ramp, rail, rod, pinion, and/or other element configured to engage with and translate relative to the mating element of the spacer member 252. As illustrated in FIG. 5, the two second mating elements 268 can each include a rail. The second mating element 268 may also define a path. The path of the second mating element 268 may be parallel to the path of the first mating element. The second mating element(s) 268 may each have different features (e.g., length, curvature, and/or angle). The second mating element 268 may be coupled perpendicularly to the fixation member 254. In other embodiments, the second mating element 268 may be at a non-perpendicular angle (e.g., less than 90°) relative to the fixation member 254. The fixation member 254 may be angled in any direction relative to the second mating element(s) 268 and/or spacer member 252. For example, the fixation member 254 may be angled towards the second side 258 (e.g., obliquely and/or anterolaterally), as illustrated in FIG. 5. In other embodiments, the fixation member 254 may be angled towards an upper surface 270 or a lower surface (not shown) of the spacer member 252. The fixation member 254 can include one or more bores 278 extending therethrough, wherein each may be configured to receive a fastener therein. Each bore 278 can include an axis 276. When the device 250 is in an assembled configuration, the axis 276 can be offset (e.g., anterolaterally and/or obliquely) from the vertical, longitudinal plane 274 by an angle β, for example, in the range of from about 5° to about 90°. In some embodiments, β may be in the range of from about 5° to about 45°. In other embodiments, β may be in the range of from about 20° to about 30°. The second mating element 268 may be statically or dynamically (e.g., pivotably and/or articulably) coupled to the fixation member 254. In use, the fixation member 254 may be configured to translate at least partially into and out of the cavity 264 of the spacer member 252. This may occur as the mating elements of the spacer member 252 and the fixation member 254 engage each other (e.g., two rails coupled to the fixation member 254 may slide along two tracks within the cavity 264 of the spacer member 252).

In some embodiments, the device may further include an actuator (not shown). The actuator may be configured to urge translation of the fixation member 254 relative to the spacer member 252. In some embodiments, the actuator may be configured to engage a tool, such as a driver. In other embodiments, the device 250 may further include a locking member (not shown). The locking member may be configured to maintain the position of the fixation member 254 relative to the spacer member 252. In some embodiments, the locking member may be configured to inhibit retraction of the fixation member 254 towards the cavity 264. In other embodiments, the mating elements may be configured to inhibit retraction of the fixation member 254. For example, the mating elements may include teeth and/or ratcheting.

Embodiments herein are also directed to methods of installing the vertebral fusion device 250. These methods can include providing the vertebral fusion device 250 in a collapsed configuration. In some embodiments, this step can include inserting the vertebral fusion device 250 between adjacent vertebrae along a lateral trajectory as described herein. In the collapsed configuration, the vertebral fusion device 250 may include a first width. In some embodiments, the first width may be equal to a width of the spacer member 252 as measured from third side 260 to the fourth side 262. An outer surface 272 of the fixation member 254 may be a first distance from the third surface 260 of the spacer member 252. Additionally, when in the collapsed configuration, at least a portion of the mating element 268 may be located within the cavity 264 of the spacer member 252. In some embodiments, the fixation member 254 may also be partially or completely located within the cavity 264. Furthermore, when in the collapsed configuration, the vertebral fusion device 250 may include outer dimensions (e.g., length, width, and/or height) that are not greater than the outer dimensions of the spacer member 252 alone. When in the collapsed configuration, the device 250 may also be fully contained within the intervertebral disc space of a patient.

These methods can also include the step of transitioning the vertebral fusion device 250 from the collapsed configuration to an expanded configuration. In the expanded configuration, the device 250 can include a second width that is greater than the first width. The outer surface 272 of the fixation member 254 may be at a second distance from the third surface 260, wherein the second distance is greater than the first distance. A portion of the mating element 268 may be located outside the cavity 264. The transitioning step can include translating (e.g., extending) the fixation member 254 away from the spacer member 252 (e.g., anteriorly). This step can be performed by directly urging the fixation member 254 away from the spacer member 252, or indirectly by engaging the actuator. In some embodiments, this step can include sliding the mating element 268 of the fixation member 254 along the mating element of the spacer member 252. In some embodiments, the fixation member 254 may translate along an axis that is not parallel to the horizontal plane of the spacer member 252. In other embodiments, the fixation member 254 may translate, rotate, and/or pivot away from the spacer member 252. In embodiments that include a locking member, these methods can also include locking the fixation member 254 in the expanded configuration.

Some methods can further include inserting a fastener into bore 278 along axis 276. In some embodiments, this step can include inserting the fastener at an angle, relative to the vertical, longitudinal plane 274, in the range of from about 5° to about 90°. In other embodiments, this step can include inserting the fastener along an anterolateral and/or oblique trajectory. Advantageously, a user may be able to install the spacer member 252 and fixation member 254 along a first trajectory, and may be able to install the fastener(s) along a second trajectory. In use, when the fastener is installed along an anterolateral and/or oblique trajectory, various anatomical structures may advantageously be avoided, as described herein.

Figure 6:
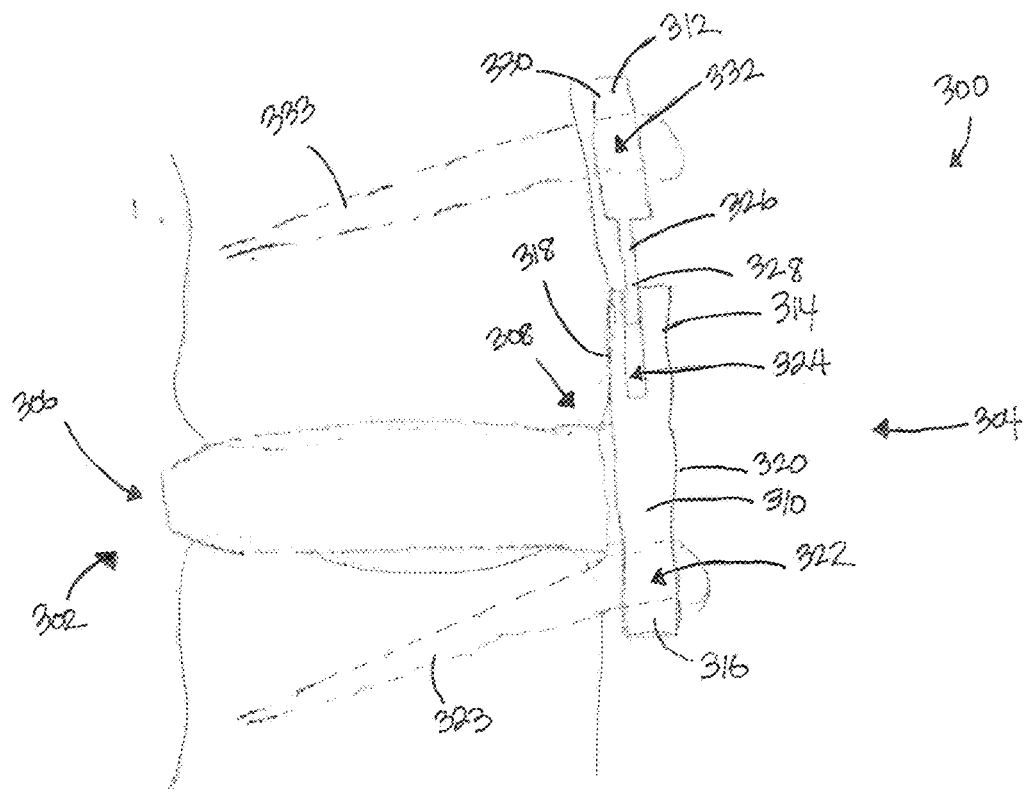
FIG. 6 illustrates a schematic view of one embodiment of a vertebral fusion device described herein.

Turning to FIG. 6, some embodiments herein are directed to a vertebral fusion device 300 that can include a spacer member 302 and a fixation member 304. The spacer member 302 can include features of the other spacer members described herein. For example, the spacer member 302 may be configured for insertion between adjacent vertebrae via a lateral procedure (e.g., lateral lumbar interbody fusion). The spacer member 302 may have a length (e.g., as measured between a leading end 306 and a trailing end 308) that is about 100-300% greater than a width thereof (e.g., as measured in the anterior-posterior direction). The spacer member 302 may also have a length that is configured to laterally span a vertebral endplate. For example, the spacer member 302 may have a length in the range of from about 40 mm to about 60 mm.

The fixation member 304 can include a base element 310 and a movable element 312. The base element 310 can include a first (e.g., superior) end 314, a second (e.g., inferior) end 316, a distal surface 318, and a proximal surface 320. The base element 310 can also include at least one bore 322 configured to receive a fastener 323 therethrough. The base element 310 can be configured to engage the spacer member 302, for example, at the trailing end 308 thereof. For example, the base element 310 can be statically or dynamically (e.g., pivotably and/or articulably) engaged with the spacer member 302. In some embodiments, the base element 310 can be integrated with the spacer member 302. In other embodiments, a coupling member, such as a set screw, can be configured to couple the base element 310 with the spacer member 302. In yet other embodiments, the base element 310 may not be engaged with the spacer member 302.

The movable element 312 can include a fastener portion 330 extending from a coupler portion 328. In some embodiments, when assembled, the fastener portion 330 may be superior to the coupler portion 328, or vice versa. The fastener portion 330 can include a bore 332 configured to receive a fastener 333 therethrough. The coupler portion 328 can be configured to couple and/or engage the base element 310. In some embodiments, the coupler portion 328 can be configured to be at least partially received within the base element 310. In other embodiments, the coupler portion 328 may be coupled to the distal surface 318 or proximal surface 320 of the base element 310.

The base element 310 may be configured to be movably coupled with the movable element 312. Accordingly, the base element 310 can include a first coupling feature 324 that can be configured to engage a second coupling feature 326 on the movable element 312. In some embodiments, the first coupling feature 324 may be disposed at the first end 314 of the base element 310. In other embodiments, the first coupling feature 324 may be disposed at the second end 316 of the base element 310. The second coupling feature 326 may be disposed on the coupler portion 328 of the movable element 312. In some embodiments, the first coupling feature 324 can include a protrusion, such as a prong, pin, bump, tongue, and/or rail, and the second coupling feature 326 can include a receptacle, such as a slot, channel, hole, groove, ledge, and/or track. In other embodiments, the first coupling feature 324 can include a receptacle and the second coupling feature 326 can include a protrusion. In yet other embodiments, the first and second coupling features 324, 326 may be coupled via a joint (e.g., a dovetail joint, a tongue and groove joint, and/or a splice joint). In some embodiments, the second coupling feature 326 may be configured to translate (e.g., slide) along the first coupling feature 324. In other embodiments, the second coupling feature 326 may be configured to pivot about the first coupling feature 324. As illustrated in FIG. 6, the first coupling feature 324 can include a slot at the first end 314 of the base element, and the second coupling feature 326 can include a flange extending from the coupler portion 328 of the movable element 312. In some embodiments, the slot at the first end 314 of the base element 310 can include the first coupling feature 324 therein. In other embodiments, the fixation member 304 can include two or more movable elements engaged with the base element 310. For example, the fixation member 304 can include an upper movable element configured to translate superiorly and/or a lower movable element configured to translate inferiorly.

In use, the fixation member 304 may be configured to reversibly transition between an extended configuration and a retracted configuration. In the retracted configuration, the fixation member 304 may have a first height. In some embodiments, the height may be measured from the fastener portion 330 of the movable element 312 to the second end 316 of the base element 310. The fastener portion 330 may be separated from the second end 316 by a first distance. In some embodiments, at least a section of the coupler portion 328 may be disposed within the base element 310. In the extended configuration, the fixation member 304 may have a second height that is greater than the first height. The fastener portion 300 may be separated from the second end 316 by a second distance that is greater than the first distance. In some embodiments, the section of the coupler portion 328 that was disposed within the base element 310 may be outside of the base element 310. In some embodiments, the device 300 may also include a locking member (not shown). In these embodiments, the locking member may be configured to inhibit extension and/or contraction of the movable element 312. For example, the locking member may include teeth, ratcheting, a fastener, and/or other blocking features.

Also described herein are methods for installing the vertebral fusion device 300. These methods can include providing the vertebral fusion device 300 in a retracted configuration as described herein. In some embodiments, this step can include inserting the device 300 between adjacent vertebrae (e.g., L4-L5 vertebrae) along a lateral trajectory. These methods can also include transitioning the fixation member 304 from the retracted configuration to the extended configuration, for example, by extending the movable element 312. In some embodiments, the movable element 312 can translate (e.g., slide) relative to the base element 310. For example, the movable element 312 can telescope at least partially out of the base element 310. In other embodiments, this step can include pivoting the movable element 312 away from the base element 310. This step can be performed by directly urging the movable element 312 away from the base element 310, for example, by sliding the movable element 312 at least partially out of the slot on the base element 310. In other embodiments, this step can be performed indirectly by activating an actuator engaged with the movable element 312. In embodiments that include a locking member, the method can also include locking the fixation member 304 in the extended configuration.

Some methods can further include inserting fastener 323 into bore 322 and/or inserting fastener 333 into bore 332. Those skilled in the art may appreciate that the dynamic capability of the movable element 312 can advantageously enable a user to adjust a position of the fastener 333 based on the particular anatomy of an individual patient. Accordingly, some methods can further include extending and/or retracting the movable element 312 multiple times so as to calibrate and/or improve the location of fastener placement.

Figure 7A:
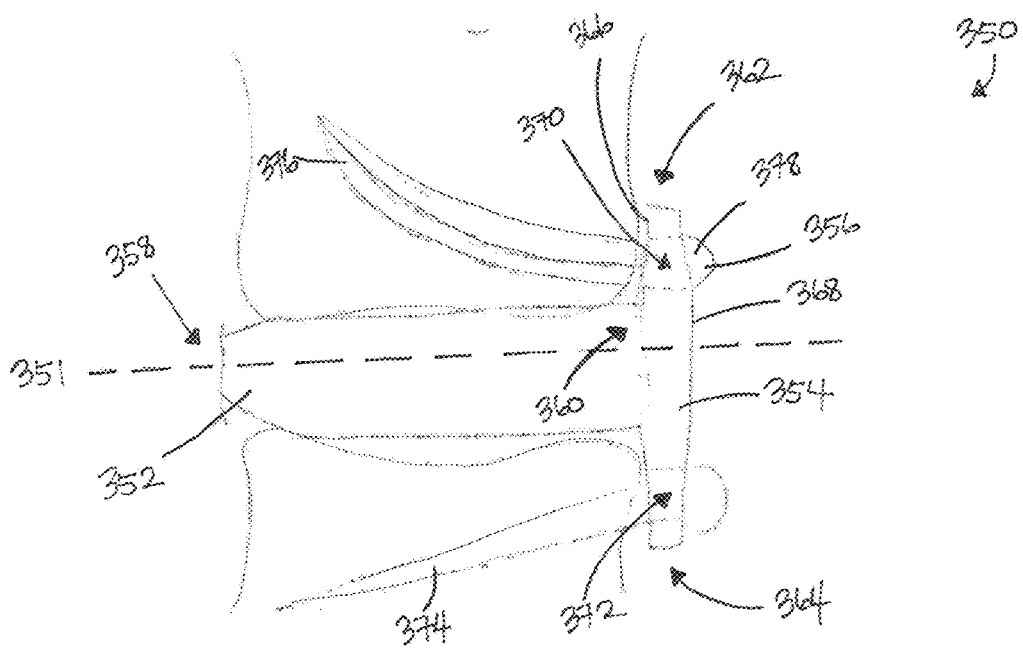
FIG. 7A illustrates a schematic view of one embodiment of a vertebral fusion device described herein.

The vertebral fusion devices described herein can be used with one or more fasteners (e.g., bone screw, anchor, and/or staple). In any of these embodiments, a curved fastener can be used. One example is illustrated in FIG. 7A. Turning now to FIG. 7A, some embodiments herein are directed to a vertebral fusion device 350 that can include a spacer member 352, a fixation member 354, and a curved fastener 356. In some embodiments, the device 350 can also include a straight fastener 374. The spacer member 352 and fixation member 354 can include some or all of the features of the spacer members and fixation members described herein. For example, the spacer member 352 may be configured for insertion between adjacent vertebrae via a lateral procedure (e.g., lateral lumbar interbody fusion). The spacer member 352 may have a length (e.g., as measured between a leading end 306 and a trailing end 308) that is about 100-300% greater than a width thereof (e.g., as measured in the anterior-posterior direction). The spacer member 352 may also have a length that is configured to laterally span a vertebral endplate. For example, the spacer member 352 may have a length in the range of from about 40 mm to about 60 mm.

The fixation member 354 can include a first (e.g., superior) end 362, a second (e.g., inferior) end 364, a distal surface 366, and a proximal surface 368. The fixation member 354 can also include at least one bore configured to receive a fastener therethrough. As illustrated in FIG. 7A, the first end 362 can include a first bore 370 and the second end 364 can include a second bore 372. The first and/or second bores 370, 372 can each include an axis (not shown). In some embodiments, at least one axis (e.g., the axis of first bore 370) can be perpendicular to the fixation member 354. In other embodiments, at least one axis can be configured to be parallel to a vertical, longitudinal plane 351 of the spacer member 352. In some embodiments, the fixation member 354 can include a height (e.g., as measured from the first end 362 to the second end 364) that is greater than a height of the base member 352. In other embodiments, the height of the fixation member 354 can be less than or equal to the height of the base member 352. In yet other embodiments, the device 350 may have a height that is configured to fit within a disc space.

The fixation member 354 can be configured to engage the spacer member 352, for example, at the trailing end 360 thereof. For example, the fixation member 354 can be statically or dynamically (e.g., pivotably and/or articulably) engaged with the spacer member 352. In some embodiments, the fixation member 354 can be integrated with the spacer member 352. In other embodiments, a coupling member, such as a set screw, can be configured to couple the fixation member 354 with the spacer member 352. In yet other embodiments, the fixation member 354 may not be engaged with the spacer member 352.

The curved fastener 356 can include a curved, elongate body 376 extending from a head 378. The elongate body 376 can be curved along a longitudinal axis thereof. In use, the elongate body 376 may be configured to curve away from the spacer member 352. The elongate body 376 may be configured to pass through a bore (e.g., first bore 370 and/or second bore 372). Accordingly, the body 376 may have a diameter and/or width that is less than a diameter of first bore 370. The curved fastener 356 can be any suitable fastener member configured to couple an implant to a bone. For example, the curved fastener 356 can include an anchor, staple, and/or screw. In some embodiments, the body 376 can be threaded. In other embodiments, the body 376 can include one or more backout-prevention members, such as teeth and/or ratcheting. The body 376 can include a tapered tip. In some embodiments, the curved fastener 356 can be cannulated. The head 378 may be enlarged and/or rounded. In other embodiments, the head 378 may be cylindrical, conical, and/or frustoconical. The head 378 may be configured to engage the fixation member 354. For example, the head may be configured to rest within one of the bores. As illustrated in FIG. 7A, curved fastener 356 can be engaged with the first (e.g., superior) bore 370 and straight fastener 374 can be engaged with the second (e.g., inferior) bore 372. In other embodiments, curved fastener 356 can be engaged with the second (e.g., inferior) bore 372 and straight fastener 374 can be engaged with the first (e.g., superior) bore 370.

Embodiments herein are also directed to methods of installing the vertebral fusion device 350. These embodiments can include providing the device 350 as described herein with respect to other vertebral fusion devices. For example, in some embodiments, this step can include inserting the device 350 into a space, such as between adjacent vertebrae (e.g., L4-L5 vertebrae), along a lateral trajectory. In some embodiments, the spacer member 352 and the fixation member 354 may be coupled prior to insertion. In other embodiments, the spacer member 352 and the fixation member 354 may be coupled after insertion (e.g., in situ). The method can also include inserting the curved fastener 356 into the first bore 370 at the first (e.g., superior) end 362 of the fixation member 354. Furthermore, the curved fastener 356 can be inserted along a curved trajectory that is coaxial with the longitudinal axis of the body 376. In some embodiments, this step can include inserting the body 376 into a superior vertebra. Those skilled in the art may appreciate that this curved trajectory in the superior vertebra may advantageously be configured to avoid certain anatomical structures as described herein.

The vertebral fusion devices described herein may include a fastener configured to follow a trajectory that has been selected and/or altered to avoid certain anatomical structures as described herein. As described herein with respect to vertebral fusion device 350, in some embodiments, a curved fastener may be included. In an alternative embodiment, illustrated in FIG. 7B, the vertebral fusion device 350 can include one, two, or more fasteners 380 configured for lateral insertion along a posterior angle. The fastener 380 can include an elongate body 382 extending from a head 384. The elongate body 382 can extend along axis 386 in a straight line. The elongate body 382 can include a length configured for insertion through bore 370 at an angle to the vertical, longitudinal plane 351. In some embodiments, the elongate body 382 may have a length that is less than that of other fasteners (e.g., curved fastener 356 and/or straight fastener 374). Those skilled in the art may appreciate that fastener insertion along a posterior angle may entail the risk of injury to various anatomical structures. However, the shorter length of elongate body 382 may advantageously enable insertion in a posterior direction while inhibiting possible injury that may be caused by a fastener protruding into the body.

Figure 7B:
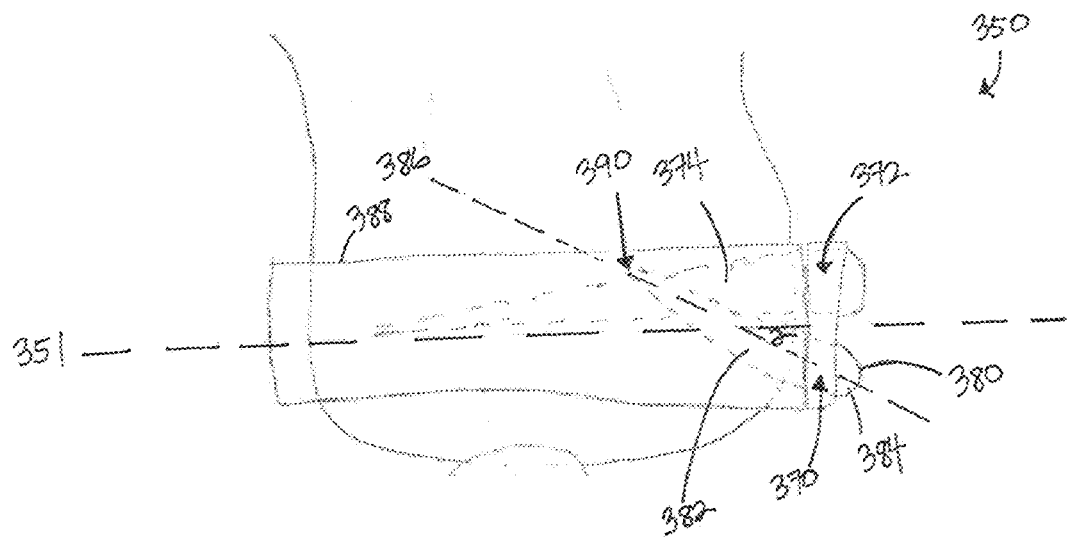
FIG. 7B illustrates a schematic view of one embodiment of a vertebral fusion device described herein.

In use, after the spacer member 352 and the fixation member 354 have been installed, the fastener 380 may be inserted into the first bore 370 in a posterior and/or posterolateral direction (e.g., towards posterior side 388 of spacer member 352). The fastener 380 may also be inserted into a superior vertebra (e.g., an L4 vertebra). As illustrated in FIG. 7B, the fastener 380 may be inserted along a trajectory such that the axis 386 intersects the vertical, longitudinal plane 351 of the spacer member 352. The axis 386 and the plane 351 may intersect to form an angle γ that can be in the range of from about 5° to about 90°. In other embodiments, γ can be in the range of from about 5° to about 45°. In yet other embodiments, γ can be in the range of from about 20° to about 30°. In some embodiments, the fastener 380 may be inserted along a trajectory such that the distal tip 390 of the fastener 380 does not protrude beyond the posterior side 388 of the spacer member 352. Those skilled in the art may appreciate that the use of fastener 380 along this posterior approach may enable placement of the fastener while avoiding certain anatomical structures as described herein. In some embodiments, a fastener (e.g., curved fastener 356, straight fastener 374, and/or fastener 380) may be also inserted into the second bore 372 and/or an inferior vertebra (e.g., an L5 vertebra).

Figure 8A:
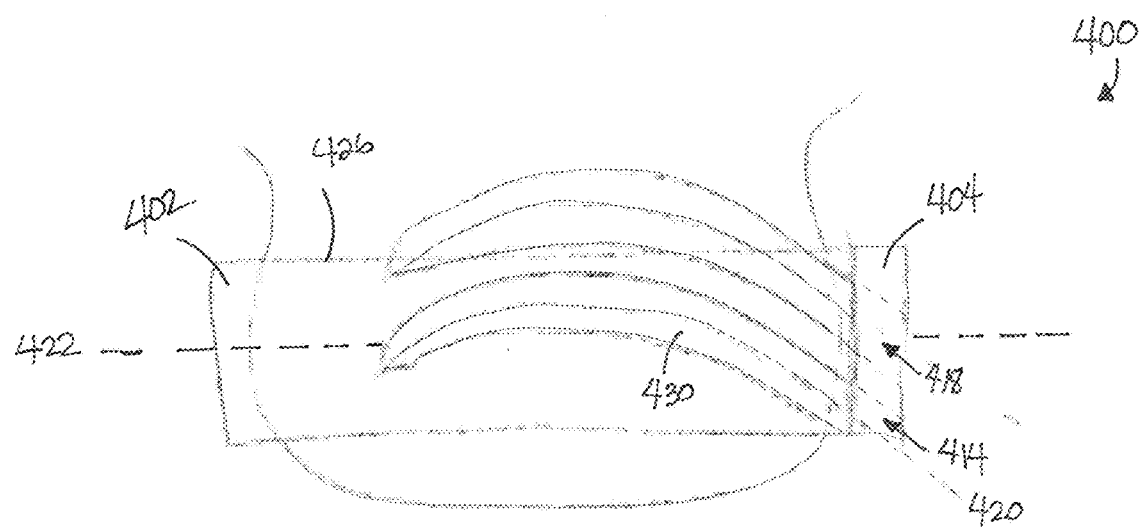
FIGS. 8A-B illustrate schematic views of one embodiment of a vertebral fusion device described herein.
Figure 8B:
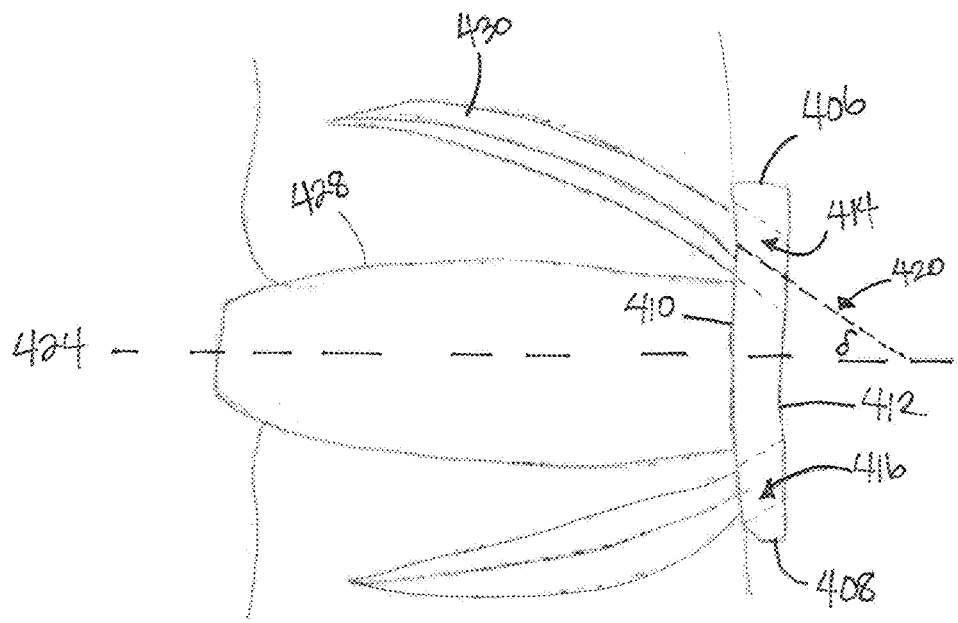

In some embodiments, one or more bores of a fixation member may be angled to direct the trajectory of a fastener. As illustrated in FIGS. 8A-B, vertebral fusion device 400 can include a spacer member 402 and a fixation member 404. The spacer member 402 and the fixation member 404 can include some or all of the features of the spacer members and fixation members described herein, unless described otherwise. As illustrated in FIG. 8B, the fixation member 404 can include a first (e.g., superior) end 406, a second (e.g., inferior) end 408, a distal surface 410, and a proximal surface 412. The first end 406 can include a first bore 414 and the second end 408 can include a second bore 416. In some embodiments, the first and/or second ends 406, 408 can include two or more bores. As illustrated in FIG. 8A, for example, the first end 406 can include first bore 414 and bore 418. The first bore 414 can include an axis 420 that can be non-perpendicularly angled relative to the spacer member 402 and/or the fixation member 404. As illustrated in FIG. 8A, axis 420 can be configured to intersect a vertical, longitudinal plane 422 of the spacer member 352. Axis 420 may extend in a posterior and/or posterolateral direction (e.g., towards posterior side 426 of spacer member 402). The axis 420 and the plane 422 may intersect to form an angle (not shown) that can be in the range of from about 5° to about 90°. In other embodiments, the angle can be in the range of from about 5° to about 45°. In yet other embodiments, the angle can be in the range of from about 20° to about 30°. As illustrated in FIG. 8B, axis 420 can also be configured to intersect a horizontal, longitudinal plane 424 of the spacer member 352. Axis 420 may extend in an upward or superior direction (e.g., away from superior surface 428 of the spacer member 402). The axis 420 and the plane 424 may intersect to form an angle δ that can be in the range of from about 5° to about 90°. In other embodiments, δ can be in the range of from about 5° to about 45°. In yet other embodiments, δ can be in the range of from about 20° to about 30°. Any other bores disposed on the fixation member 404 (e.g., bore 418) can include an axis having a similar trajectory as described with respect to axis 420.

In use, after the spacer member 402 and the fixation member 404 have been installed, a fastener 430 may be inserted into the first bore 414 along axis 420. As illustrated in FIGS. 8A-B, a curved fastener (e.g., curved fastener 356) may be inserted therein. In other embodiments, a straight fastener may be used. The fastener may be a screw, anchor, and/or staple. The fastener may be inserted from an anterolateral and/or oblique position, and may extend posteriorly and/or posterolaterally. Advantageously, the angled axis 420 of bore 414 can direct a fastener away from certain anatomical structures as described herein, including, without limitation, the iliac crest, psoas major, dura, and/or lumbar plexus.

Figure 9:
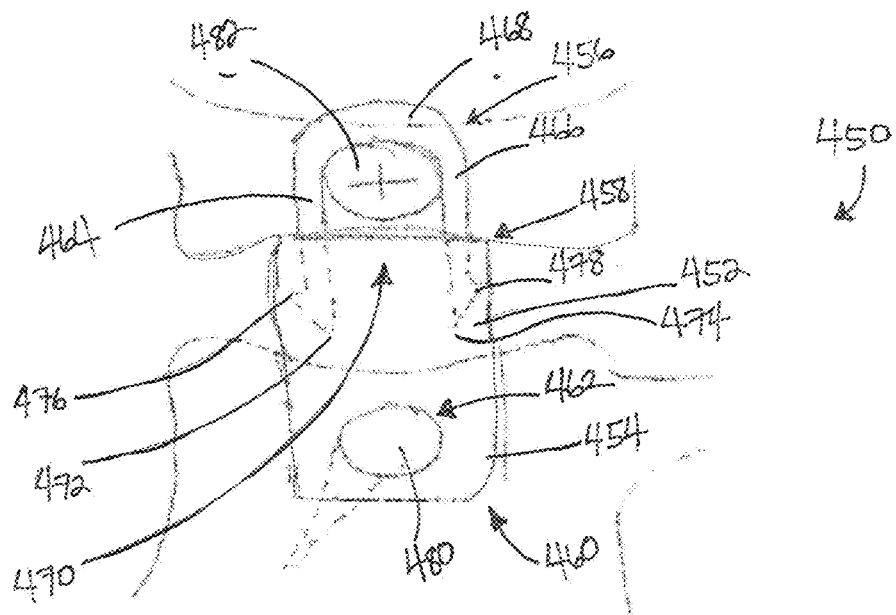
FIG. 9 illustrates a schematic view of one embodiment of a vertebral fusion device described herein.

Turning now to FIG. 9, an alternative embodiment of a vertebral fusion device is illustrated. Vertebral fusion device 450 can include a spacer member 452, a fixation member 454, and a clamp member 456. The spacer member 452 and fixation member 454 can include some or all of the features of the spacer members and fixation members described herein. For example, the spacer member 452 may be configured for insertion between adjacent vertebrae via a lateral procedure (e.g., lateral lumbar interbody fusion). The spacer member 452 may have a length (e.g., as measured between a leading end and a trailing end) that is about 100-300% greater than a width thereof (e.g., as measured in the anterior-posterior direction). The spacer member 452 may also have a length that is configured to laterally span a vertebral endplate. For example, the spacer member 452 may have a length in the range of from about 40 mm to about 60 mm. The spacer member 452 can also include a plurality of horizontal grooves at a trailing end thereof. In some embodiments, the grooves can be disposed on a proximal surface and/or on an inner surface of the spacer member 452. Each groove can include a non-symmetrical slope. For example, each groove can be slanted, tapered, and/or sawtooth-shaped. The grooves can be configured to engage the clamp member 456 as described further herein.

In some embodiments, the spacer member 452 may be configured to engage the fixation member 454. The fixation member 454 can include a first (e.g., superior) end 458 and a second (e.g., inferior) end 460. The fixation member 454 can also include at least one bore configured to receive a fastener therethrough. As illustrated in FIG. 9, the second end 460 can include a single bore 462 therethrough. In some embodiments, the fixation member 454 may include only one bore. In other embodiments, the first end 458 may not include any bores. In yet other embodiments, the second end 460 may not include any bores. In some embodiments, the fixation member 454 can include a height (e.g., as measured from the first end 458 to the second end 460) that is greater than a height of the spacer member 452. In other embodiments, the height of the fixation member 454 can be less than or equal to the height of the spacer member 452. In yet other embodiments, the device 450 may have a height that is configured to fit within a disc space (e.g., between two adjacent vertebrae).

The clamp member 456 can include first and second prongs 464, 466 extending generally perpendicularly from a body portion 468. The body portion 468 can be straight or curved. In some embodiments, the body portion 468 may be curved. In some embodiments, the body portion 468 may include a radius of curvature that is greater than that of a fastener body and not larger than that of a fastener head. The body portion 468 and first and second prongs 464, 466 may define a U-shaped opening 470. Each prong 464, 466 can include a tip 472, 474 having a retention feature 476, 478 thereon. The retention feature 476, 478 may include a projection angled away from the tip, such as a sawtooth, barb, or ratchet. The retention feature 476, 478 may be configured to engage the grooves on the spacer member 452.

Also described herein are methods for installing the vertebral fusion device 450. These embodiments can include providing the device 450 as described herein with respect to other vertebral fusion devices. For example, in some embodiments, this step can include inserting the device 450 into a space, such as between adjacent vertebrae (e.g., L4-L5 vertebrae), along a lateral trajectory. In some embodiments, the spacer member 452 and the fixation member 454 may be coupled prior to insertion. In other embodiments, the spacer member 452 and the fixation member 454 may be coupled after insertion (e.g., in situ). A fastener 480 can be inserted into the bore 462 on the second end 460 of the fixation member 454. Any of the fasteners described herein can be used. In some embodiments, this step can include inserting the fastener 480 into an inferior vertebra.

Methods described herein can also include placing the clamp member 456 above the fixation member 454. In some embodiments, this step can include superficially placing the clamp member 456 on a surface (e.g., a lateral surface) of a superior vertebra. A fastener 482 can then be inserted within the U-shaped opening 470 of the clamp member 456. The fastener 482 may also be inserted above the fixation member 454. Those skilled in the art may appreciate that the fastener 482 may not be inserted into a bore in the fixation member. Advantageously, this feature may provide a user with greater flexibility with regarding fastener placement. The methods can also include translating (e.g., compressing) the clamp member 456 towards the spacer member 452 until the retention features 476, 478 of the clamp member 456 engage the grooves on the spacer member 452. Those skilled in the art may appreciate that features of the clamp member 456 and the spacer member 452 may form a ratcheting mechanism, wherein the grooves of the spacer member 452 enable translation of the clamp member 456 towards spacer member (e.g., in an inferior and/or downward direction) and inhibit translation of the clamp member 456 in the reverse direction (e.g., superior and/or upward). Additionally, the head of the fastener member 482 may inhibit lateral motion of the clamp member 456. In other embodiments, those skilled in the art may appreciate that the fixation member 454 can include a bore at the first end 458 only, and the clamp member 456 can be placed below the fixation member 454 (e.g., on an inferior vertebra).

Figure 10A:
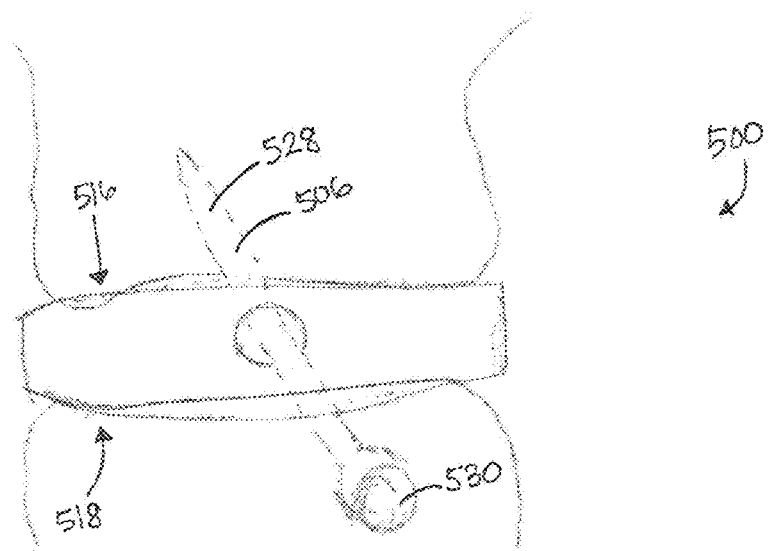
FIGS. 10A-B illustrate schematic views of one embodiment of a vertebral fusion device described herein.
Figure 10B:
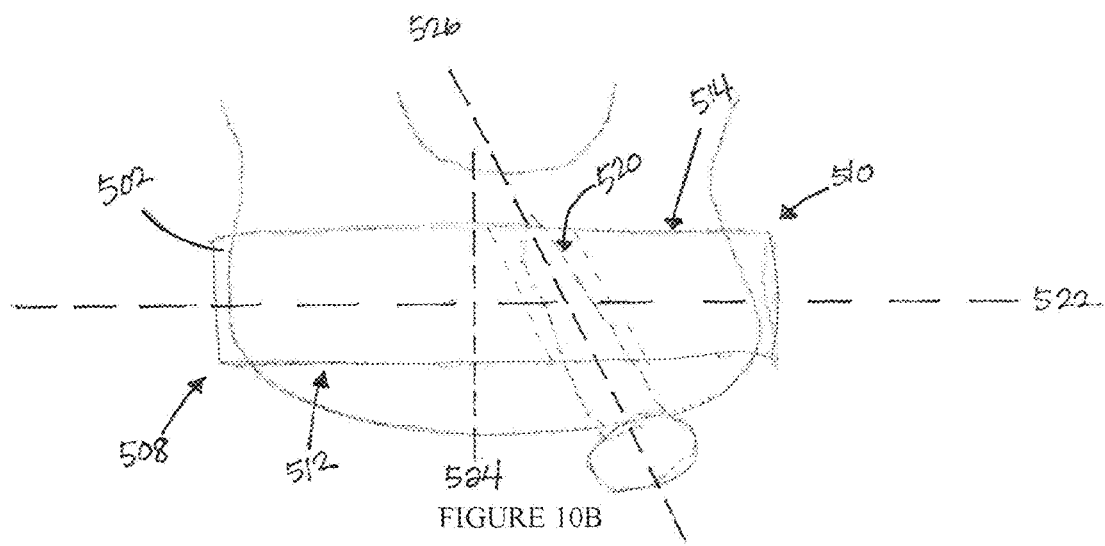

Turning to FIGS. 10A-B, an alternative embodiment of a vertebral fusion device is illustrated. Vertebral fusion device 500 can include a spacer member 502. The vertebral fusion device 500 can also include a fastener 506. The spacer member 502 can include some or all of the features of the spacer members described herein, unless described otherwise. As illustrated in FIGS. 10A-B, the spacer member 502 can include a leading end 508, a trailing end 510, a first (e.g., anterior) side 512, a second (e.g., posterior) side 514, an upper (e.g., superior) side 516, and a lower (e.g., inferior) side 518. The spacer member 502 may be configured for insertion between adjacent vertebrae via a lateral procedure (e.g., lateral lumbar interbody fusion). The spacer member 502 may have a length (e.g., as measured between leading end 508 and trailing end 510) that is about 100-300% greater than a width thereof (e.g., as measured in the anterior-posterior direction). The spacer member 502 may also have a length that is configured to laterally span a vertebral endplate. For example, the spacer member 502 may have a length in the range of from about 40 mm to about 60 mm.

The spacer member 502 may also include a receptacle 520 (e.g., a bore and/or channel) configured to receive at least a portion of fastener 506 therethrough, as illustrated in FIG. 10B. In some embodiments, the receptacle 520 can include an opening on the upper and/or lower sides 516, 518. In other embodiments, the receptacle 520 can include an opening on the first and/or second sides 512, 514. The receptacle 520 can include an axis 526. In some embodiments, the axis 526 can be generally straight; in other embodiments, the axis 526 can be generally curved. As illustrated in FIG. 10B, the axis 526 can be offset from a vertical plane (e.g., longitudinal vertical plane 522 and/or transverse vertical plane 524) of the spacer member 502. The axis 526 may be offset from a vertical plane of the spacer member 502 by an angle in the range of from about 5° to about 90°. In some embodiments, the axis 526 may be offset from a vertical plane of the spacer member 502 by an angle in the range of from about 5° to about 45°. In other embodiments, the axis 526 may be offset from a vertical plane of the spacer member 502 by an angle in the range of about 20° to about 30°. In some embodiments, the axis 526 can intersect a vertical plane of the spacer member 502. The spacer member 502 can include a locking member and/or a retention member, such as ratcheting, teeth, barbs, and/or blades, which can be configured to retain the fastener 506 therein.

The vertebral fusion device 500 may or may not include a fixation member (not shown). In some embodiments, the spacer member 502 may be configured to engage a fixation member. In some embodiments, the fixation member may be configured to engage one or more areas of the spacer member 502, such as the leading end 508, trailing end 510, first side 512, second side 514, upper side 516, and/or lower side 518. In some embodiments, the fixation member may be configured to engage an outer surface of the spacer member 502. In other embodiments, the fixation member may be configured to engage an inner surface of the spacer member 502. The fixation member can include one or more dimensions (e.g., length, width, and/or height) that are not larger than that of the spacer member 500. The fixation member may be generally flat and/or planar. The fixation member may include a bore passing therethrough, and may be configured to receive the fastener 506 therein.

The spacer member 502 may be configured to engage (e.g., receive) the fastener 506. As illustrated in FIG. 10A, the fastener 506 can include an elongate body 528 extending from a head 530. The fastener 506 can include a screw, anchor, and/or staple. The fastener 506 can include one or more features of the fasteners described herein. The elongate body 528 can be threaded. The elongate body 528 can be configured to pass through the bore 520 of the spacer member 502. The elongate body 528 can have a length that can be configured to be greater than an intervertebral space, as illustrated in FIG. 10A. The length of the elongate body 528 can be greater than the height of the spacer member 502. As illustrated in FIG. 10A, the elongate body 528 can be configured to engage two adjacent vertebral bodies.

Embodiments herein are also directed to methods of installing the vertebral fusion device 500. These methods can include providing the device 500 as described herein with respect to other vertebral fusion devices. For example, in some embodiments, this step can include inserting the device 500 into a space, such as between adjacent vertebrae (e.g., L4-L5 vertebrae), along a lateral trajectory. Methods described herein can also include the step of inserting the fastener 506 through the bore 520 of the spacer member 502. In some embodiments, when the fastener 506 is inserted, it can extend above and below the device 500 (e.g., beyond upper and lower sides 516, 518). In other embodiments, when the fastener 506 is inserted, it can be located within a perimeter of the device 500 (e.g., within the leading end 508, trailing end 510, first side 512, and second side 514). In some embodiments, this step can include inserting the fastener 506 through an inferior vertebra, the device 500, and a superior vertebra. In other embodiments, this step can include inserting the fastener 506 through a superior vertebra, the device 500, and an inferior vertebra. In some embodiments, the fastener 506 can be inserted from an anterolateral and/or oblique position (e.g., between a direct lateral and direct anterior point of entry). In other embodiments, the fastener 506 can be inserted from a position anterior to the iliac crest. Advantageously, those skilled in the art may appreciate that these approaches may enable retention of the device 500 between adjacent vertebral bodies while avoiding certain anatomical structures. Some embodiments can also include locking the fastener 506 relative to the spacer member 502. This step can include actuating the locking member. In other embodiments, a retention member may retain the fastener 506 relative to the spacer member 502 without a separate actuation step.

Figure 11A:
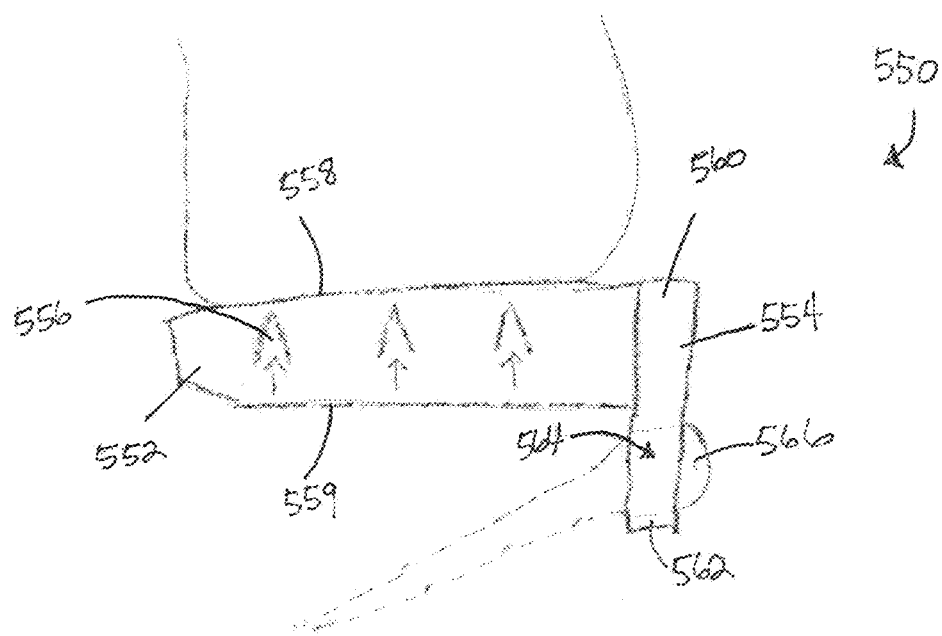
FIGS. 11A-B illustrate schematic views of one embodiment of a vertebral fusion device described herein.
Figure 11B:
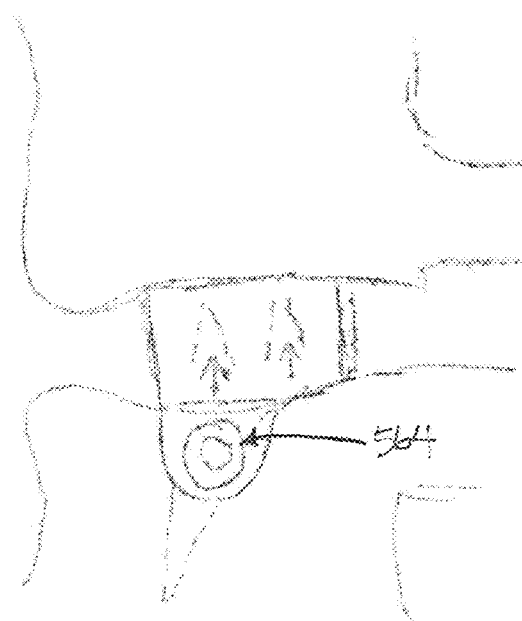

Turning now to FIGS. 11A-B, an alternative embodiment of a vertebral fusion device is illustrated. Vertebral fusion device 550 can include a spacer member 552 and a fixation member 554. The spacer member 552 and the fixation member 554 can include some or all of the features of the spacer members and fixation members herein, unless described otherwise. For example, the spacer member 552 may be configured for insertion between adjacent vertebrae via a lateral procedure (e.g., lateral lumbar interbody fusion). The spacer member 552 may have a length (e.g., as measured between a leading end and a trailing end) that is about 100-300% greater than a width thereof (e.g., as measured in the anterior-posterior direction). The spacer member 552 may also have a length that is configured to laterally span a vertebral endplate. For example, the spacer member 552 may have a length in the range of from about 40 mm to about 60 mm. As illustrated in FIGS. 11A-B, the spacer member 552 can also include one or more retention members 556. In some embodiments, the spacer member 552 can include a plurality of retention members 556. Each retention member 556 can be configured to urge, encourage, and/or retain the vertebral fusion device 550 within an intervertebral space. In some embodiments, each retention member 556 can include a spike, anchor, and/or shim. Advantageously, the retention member(s) 556 can be deployable, extendable, and/or expandable. In some embodiments, the retention member(s) 556 may be located within the spacer member 552. Each retention member 556 may be configured to transition between a retracted state, wherein the retention member 556 is contained within the spacer member 552, to a deployed state, wherein at least a portion of the retention member 556 is protruding beyond the spacer member 552. In some embodiments, the spacer member 552 can include one or more holes, for example, on upper surface 558, through which the retention member(s) 556 can pass. In other embodiments, the device 550 can further include an actuator (not shown) that can be configured to deploy and/or retract the retention member(s) 556.

In some embodiments, the spacer member 552 may be configured to engage the fixation member 554. In these embodiments, the fixation member 554 may be configured to statically or dynamically (e.g., pivotably and/or articulably) engage the spacer member 552 as described herein. The fixation member 554 can include a first (e.g., superior) end 560 and a second (e.g., inferior) end 562. The fixation member 554 can also include at least one bore configured to receive a fastener therethrough. As illustrated in FIGS. 11A-B, the second end 562 can include a single bore 564 therethrough. In some embodiments, the fixation member 554 may include only one bore. In other embodiments, the first end 560 may not include any bores. In yet other embodiments, the second end 562 may not include any bores. In some embodiments, the fixation member 554 can include a height (e.g., as measured from the first end 560 to the second end 562) that is greater than a height of the spacer member 552 (e.g., as measured between the upper surface 558 and lower surface 559). In other embodiments, the height of the fixation member 554 can be less than or equal to the height of the spacer member 552. When in an assembled configuration, as illustrated in FIGS. 11A-B, the first end 560 may not extend beyond the upper surface 558 of the spacer member 552, while the second end 562 may extend beyond the lower surface 559 of the spacer member 552.

Also described herein are methods for installing the vertebral fusion device 550. These embodiments can include providing the device 550 as described herein with respect to other vertebral fusion devices. For example, in some embodiments, this step can include inserting the device 550 into a space, such as between adjacent vertebrae (e.g., L4-L5 vertebrae), along a lateral trajectory. In some embodiments, the spacer member 552 and the fixation member 554 may be coupled prior to insertion. In other embodiments, the spacer member 552 and the fixation member 554 may be coupled after insertion (e.g., in situ). The vertebral fusion device 550 may be provided with the retention member(s) 556 in a retracted configuration. In this configuration, the retention member(s) 556 may be retained within the spacer member 552. A fastener 566 can be inserted into the bore 564 on the second end 562 of the fixation member 554. Any of the fasteners described herein can be used. In some embodiments, this step can include inserting the fastener 566 into an inferior vertebra. The methods can also include transitioning the retention member(s) 556 from the retracted configuration to the deployed configuration. This step can include deploying, extending, and/or expanding the retention member(s) 556 so that they are at least partially protruding beyond an outer surface (e.g., upper surface 558) of the spacer member 552. This step can also include engaging (e.g., gripping, biting, penetrating, and/or piercing) a superior vertebra with the retention member(s) 556. Those skilled in the art may appreciate that because the device 550 uses internal retention member 556 to engage the superior vertebra, a user advantageously may avoid interference from the iliac crest and other anatomical features.

Figure 12A:
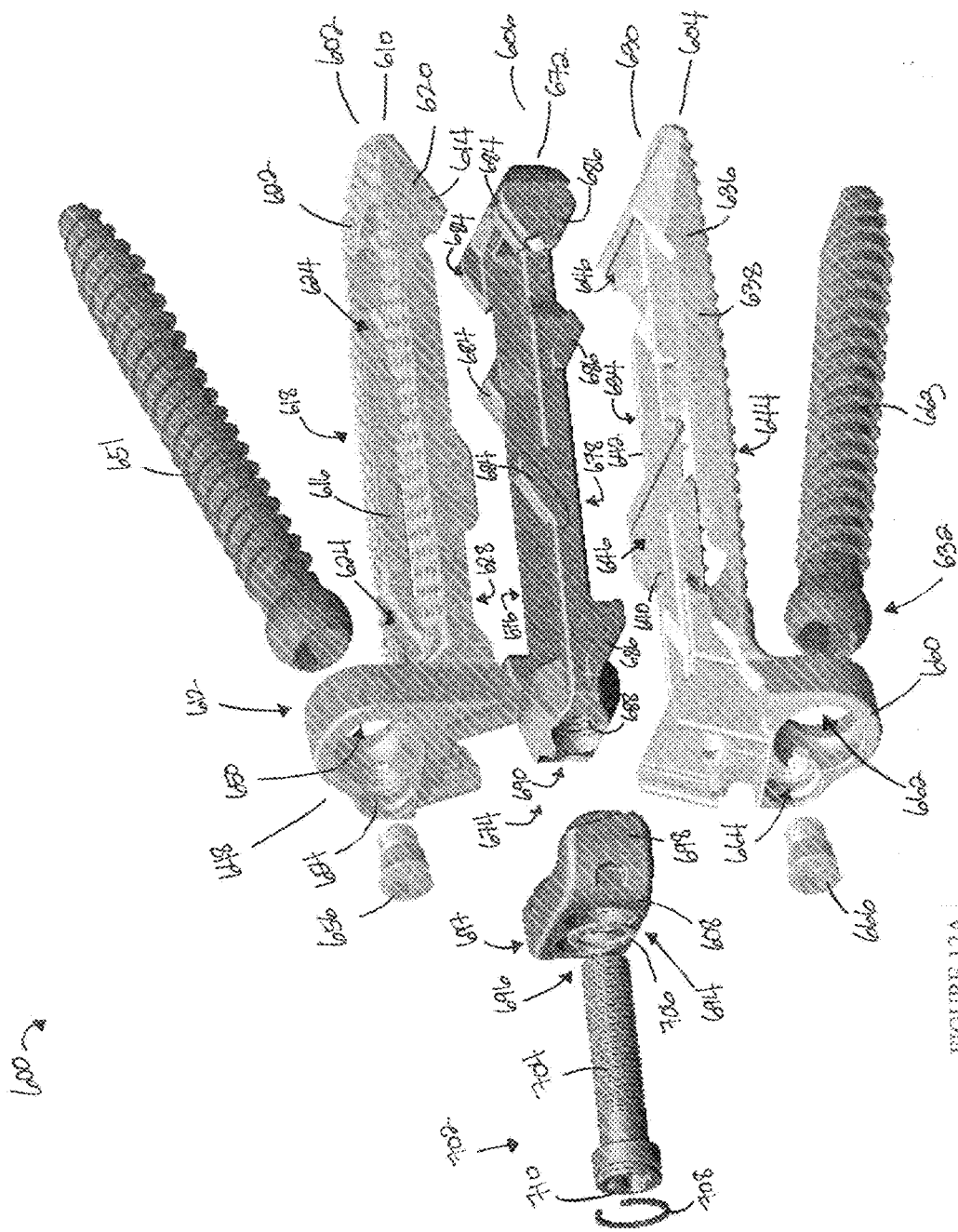
FIGS. 12A-B illustrate exploded views of one embodiment of a vertebral fusion device described herein.
Figure 12B:
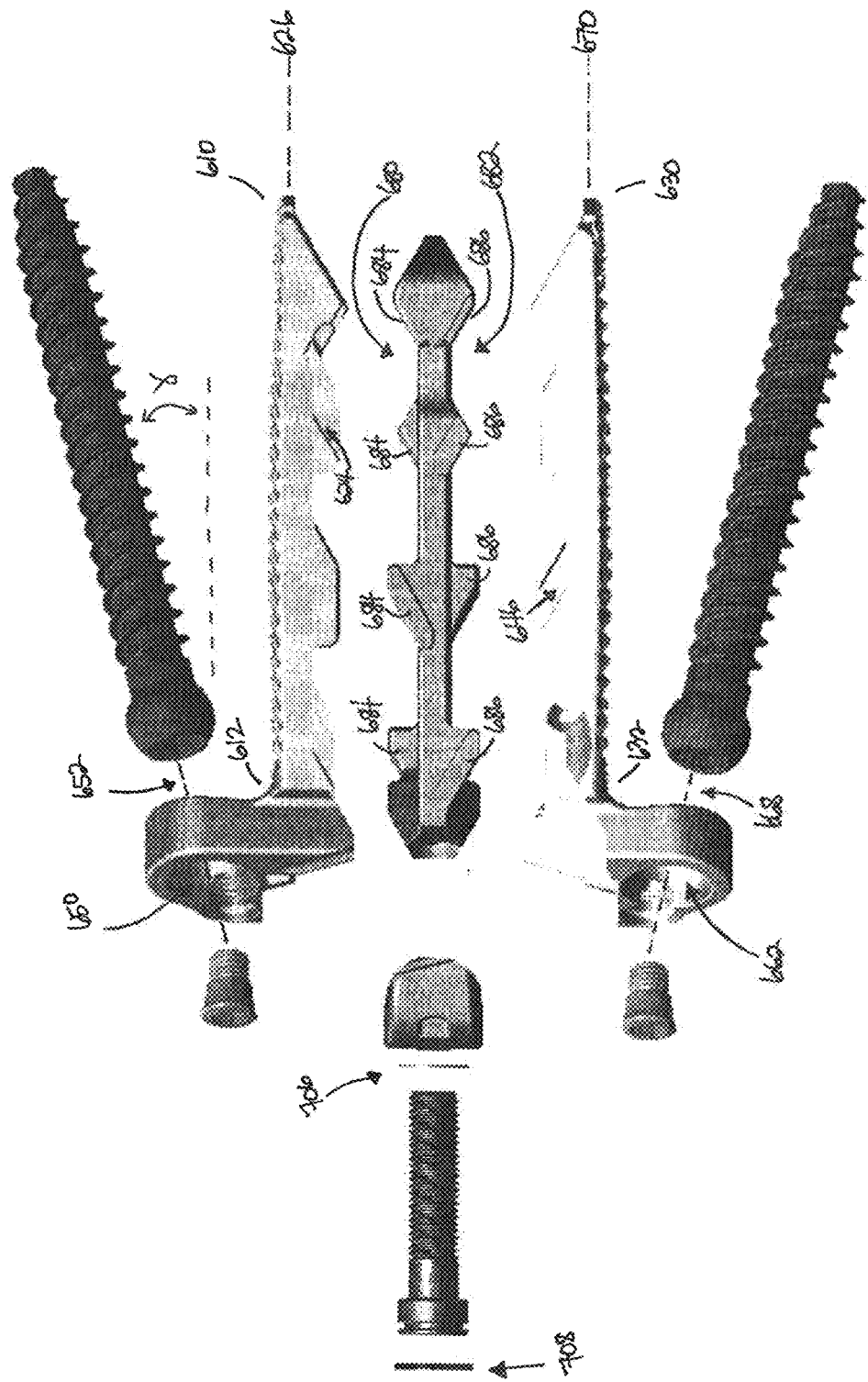
Figure 12C:
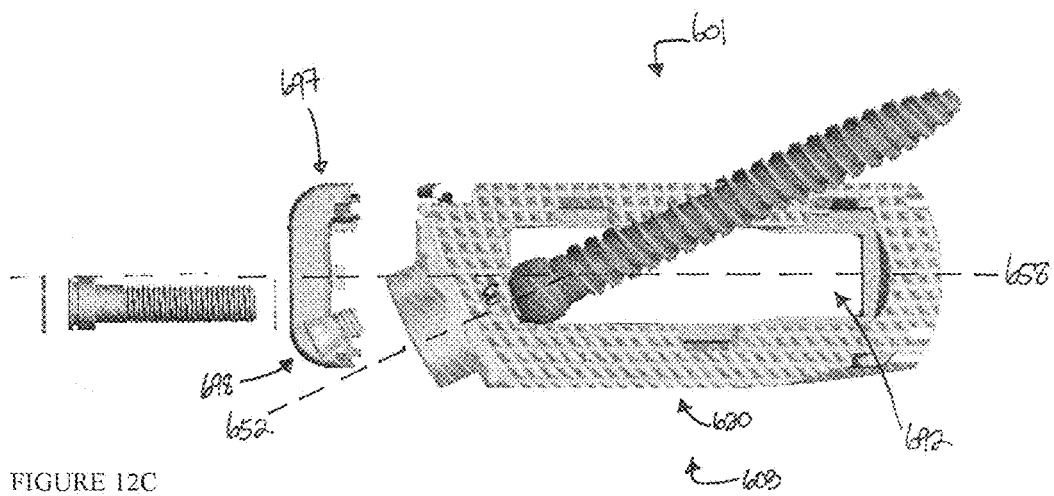
FIGS. 12C-D illustrate perspective views of one embodiment of a vertebral fusion device described herein.

Turning now to FIGS. 12A-F, an alternative embodiment of a vertebral fusion device is illustrated. Unless otherwise described herein, vertebral fusion device 600 can include some or all of the features of the vertebral fusion devices described in U.S. patent application Ser. No. 14/449,428, entitled "VARIABLE LORDOSIS SPACER AND RELATED METHODS OF USE," filed Aug. 1, 2014, U.S. Patent Publication No. 2014/0163683, entitled "EXPANDABLE VERTEBRAL IMPLANT," published Jun. 12, 2014, and U.S. Patent Publication No. 2013/0023993, entitled "EXPANDABLE FUSION DEVICE AND METHOD OF INSTALLATION THEREOF," published Jan. 23, 2013, all of which are hereby incorporated by reference herein in their entireties for all purposes. Vertebral fusion device 600 can include a first (e.g., upper and/or superior) endplate 602, a second (e.g., lower and/or inferior) endplate 604, a first engagement, angled, or ramped body 606, and a second engagement, angled or ramped body 608. As illustrated in FIG. 12C, the device 600 can also include a first side 601 and a second side 603. As described further herein, vertebral fusion device 600 can include an adjustable height and/or lordotic angle. In these embodiments, the first and/or second endplates 602, 604 may be configured to pivot about a pivot point, as described herein with respect to vertebral fusion device 800. The vertebral fusion device 600 may be wedge-shaped along a latitudinal axis. For example, the device 600 may have a height that increases from the first side 601 to the second side 603. In some embodiments, the first and/or second ramped bodies 606, 608 may be wedge-shaped.

First endplate 602 can include a body portion that can include a first (e.g., leading and/or distal) end 610 a second (e.g., trailing and/or proximal) end 612, a first (e.g., posterior) side 618, and a second (e.g., anterior) side 620. The body portion of the first endplate 602 can also include an outer surface 614, an inner surface 616, an upper surface 622, and a lower surface 628. As illustrated in FIG. 12A, the upper surface 622 can include a plurality of protrusions (e.g., bumps, teeth, and/or peaks) configured to engage a vertebral body. The upper surface 622 can be generally planar, concave, and/or convex. The first endplate 602 can include one or more mating features 624. In some embodiments, the mating feature(s) 624 may be located on the inner surface 616. In other embodiments, the first side 618 may include at least one mating feature 624, and the second side 620 may include at least one mating feature 624. In yet other embodiments, the first and/or second sides 618, 620 can each include a mating feature at the first end 610, a mating feature at an intermediate portion, and a mating feature at the second end 612.

As illustrated in FIG. 12A, the first endplate 602 can also include a first extension portion 648. The first extension portion 648 can extend, e.g., vertically, from the second end 612 of the body portion of the first endplate 602. The first extension portion 648 can have a height that is greater than a height of the body portion of the first endplate 602. For example, the first extension portion 648 may extend beyond the upper surface 622. In some embodiments, the first extension portion 648 may be coupled (e.g., attached, joined, and/or connected) to the first endplate 602. In some embodiments, the first extension portion 648 may be moveably (e.g., articulably) coupled to the body portion of the first endplate 602, for example, as described herein with respect to vertebral fusion device 50. For example, the body portion of the first endplate 602 and the extension portion 648 may together form a dovetail joint. In some embodiments, the first extension portion 648 and the body portion of first endplate 602 may each include a different material (e.g., a metal and/or a polymer). In other embodiments, the first extension portion 648 and the body portion of the first endplate 602 may form a unitary body. The first extension portion 648 can include a bore 650 passing therethrough. The bore 650 can be configured to receive a fastener 651 therein. The first extension portion 648 can also include a receptacle 654. The receptacle 654 may at least partially overlap the bore 650. The receptacle 654 may be configured to receive a retention member 656 therein.

As illustrated in FIG. 12B, the bore 650 can include an axis 652. In some embodiments, axis 652 may be generally parallel to a longitudinal axis (e.g., midline) 626 of the first endplate 602. In other embodiments, axis 652 may be skewed relative to the longitudinal midline 626. In yet other embodiments, axis 652 may be configured to intersect a vertical, longitudinal plane 658 of the assembled device 600, as illustrated in FIG. 12C. In some embodiments, the axis 652, bore 650, and/or first extension portion 648 may be horizontally offset from the longitudinal midline 626 and/or vertical, longitudinal plane 658. In some embodiments, the axis 652, bore 650, and/or first extension portion 648 may be horizontally offset towards the second side 620. As illustrated in FIG. 12C, the axis 652 can intersect the plane 658 by an angle ε. In some embodiments, ε can be in the range of from about 0° to about 90°. In other embodiments, ε can be in the range of from about 5° to about 45°. In yet other embodiments, ε can be in the range of from about 20° to about 30°. In some embodiments, another angle γ can be provided, as shown in FIG. 12B. In some embodiments, axis 652 can be arranged from 0-90 degrees off angle γ.

Second endplate 604 can include some or all of the same features as the first endplate 602. In some embodiments, the first and second endplates 602, 604 may be symmetrical with respect to each other. As illustrated in FIG. 12A, second endplate 604 can include a body portion that can include a first (e.g., leading and/or distal) end 630, a second (e.g., trailing and/or proximal) end 632, a first (e.g., posterior) side 634, and a second (e.g., anterior) side 636. The body portion of the second endplate 604 can also include an outer surface 638, an inner surface 640, an upper surface 642, and a lower surface 644. The lower surface 644 can include a plurality of protrusions (e.g., bumps, teeth, and/or peaks) configured to engage a vertebral body. The lower surface 644 can be generally planar, concave, and/or convex. The second endplate 604 can include one or more mating features 646. In some embodiments, the mating feature(s) 646 may be located on the inner surface 640. In other embodiments, the first side 634 may include at least one mating feature 646, and the second side 636 may include at least one mating feature 646. In yet other embodiments, the first and/or second sides 634, 636 can each include a mating feature at the first end 630, a mating feature at an intermediate portion, and a mating feature at the second end 632.

As illustrated in FIG. 12A, the second endplate 604 can also include a second extension portion 660. The second extension portion 660 can extend, e.g., vertically, from the second end 632 of the body portion of the second endplate 604. The second extension portion 660 can have a height that is greater than a height of the body portion of the second endplate 604. For example, the second extension portion 660 may extend beyond the lower surface 644. In some embodiments, the second extension portion 660 may be coupled (e.g., attached, joined, and/or connected) to the body portion of the second endplate 604. In some embodiments, the second extension portion 660 may be articulably coupled to the body portion of the second endplate 604, for example, as described herein with respect to vertebral fusion device 50. For example, the body portion of the second endplate 604 and the second extension portion 660 may together form a dovetail joint. In some embodiments, the second extension portion 660 and the body portion of the second endplate 604 may each include a different material (e.g., a metal and/or a polymer). In other embodiments, the second extension portion 660 and the body portion of the second endplate 604 may form a unitary body. The second extension portion 660 can include a bore 662 passing therethrough. The bore 662 can be configured to receive a fastener 663 therein. The second extension portion 660 can also include a receptacle 664. The receptacle 664 may at least partially overlap the bore 662. The receptacle 664 may be configured to receive a retention member 666 therein.

As illustrated in FIG. 12B, the bore 662 can include an axis 668. In some embodiments, axis 668 may be generally parallel to a longitudinal axis (e.g., midline) 670 of the second endplate 604. In other embodiments, axis 668 may be skewed relative to the longitudinal midline 670. In yet other embodiments, axis 668 may be configured to intersect a vertical, longitudinal plane (not shown) of the second endplate 604, which may be coplanar with the vertical, longitudinal plane 658 of the first endplate 602. In some embodiments, the axis 668, bore 662, and/or second extension portion 660 may be horizontally offset from the longitudinal midline 670 and/or vertical, longitudinal plane. In some embodiments, the axis 668, bore 662, and/or second extension portion 660 may be horizontally offset towards the second side 636. In some embodiments, the axis 668 can intersect the plane (e.g., including plane 658) by an angle. In some embodiments, the angle can be in the range of from about 0° to about 90°. In other embodiments, the angle can be in the range of from about 5° to about 45°. In yet other embodiments, the angle can be in the range of from about 20° to about 30°. In still other embodiments, the angle can be equal to ε as described herein.

As illustrated in FIG. 12B, mating feature 624 of the first endplate 602 may be inclined (e.g., may extend from lower surface 628 towards upper surface 622) along longitudinal axis 626 in a direction from the second end 612 towards the first end 610. In some embodiments, mating feature 624 may be angled, e.g., towards the first end 610. In other embodiments, mating feature 624 may be inclined along the longitudinal axis 626 in a direction from the first end 610 towards the second end 612. In some embodiments, mating feature 646 of the second endplate 604 may be declined (e.g., may extend from upper surface 642 towards lower surface 644) along longitudinal axis 670 in a direction from the second end 632 towards the first end 640. In some embodiments, mating feature 646 may be angled, e.g., towards the first end 630. In other embodiments, mating feature 646 may be declined along the longitudinal axis 670 from the first end 630 towards the second end 632.

As described further herein, the first and/or second endplates 602, 604 may be configured to engage (e.g., mate with) the first ramped body 606. As illustrated in FIG. 12A, the first ramped body 606 can include a first (e.g., leading and/or distal) end 672, a second (e.g., trailing and/or proximal) end 674, a first (e.g., posterior) side portion 676, and a second (e.g., anterior) side portion 678. As illustrated in FIG. 12B, the first ramped body 606 can also include a third (e.g., superior) end 680 and a fourth (e.g., inferior) end 682. The third end 680 may include one or more mating features 684 configured to engage the first endplate 602 and the fourth end 682 may include one or more mating features 686 configured to engage the second endplate 604. The first side portion 676 and/or the second side portion 678 can include one or more mating features 684, 686 configured to engage the first and/or second endplates 602, 604. In some embodiments, the first end 672 can include two or more mating features 684 on the third end 680 and two or more mating features 686 on the fourth end 682. Each of the mating features of the first ramped body 606 may be configured (e.g., shaped) to mate with a corresponding mating feature 624, 646 on the first and/or second endplates 602, 604. Mating features 684, 686 may have substantially similar inclinations, when in an assembled configuration, as their corresponding mating features 624, 646. In some embodiments, each mating feature 684 is inclined towards the first end 672 of the first ramped body 606, and each mating feature 686 is declined towards the first end 672 of the first ramped body 606. In other embodiments, mating feature 684 and mating feature 686 may diverge from each other along a longitudinal axis from a position relatively adjacent to the second end 674 to a position relatively adjacent to the first end 672. In yet other embodiments, the mating features 684, 686 may be angled, e.g., towards the first end 672. In still other embodiments, one or more mating features 684 may be inclined towards the second end 674 of the ramped body 606 and/or one or more mating features 686 may be declined towards the second end 674 of the ramped body 606. In some embodiments, one or more mating features 684, 686 can include a protrusion (e.g., a tongue, rail, and/or shoulder). In other embodiments, one or more mating features 684, 686 can include a recess (e.g., a groove, track, and/or channel). In some embodiments, for example, as illustrated in FIG. 12B, the mating features 684, 686 can alternate longitudinally along the first and/or second sides 676, 678. In other embodiments, for example, as illustrated in FIG. 12 B, the mating features 684, 686 can alternate transversely along the first and/or second sides 676, 678. Each mating feature 684 on the first ramped body 606 can be generally the same. Each mating feature 686 may be generally the same. In some embodiments, at least one mating feature 684 and/or 686 may include different properties as compared to the other mating features 684, 686.

The mating features 624, 646 on the first and/or second endplates 602, 604 as described herein may be configured to form a slidable joint with a corresponding mating feature 684 686 on the first ramped body 606. Accordingly, the first ramped body 606 may be configured to slideably engage the first and/or second endplates 602, 604. The slideable joint may advantageously enable the vertebral fusion device 600 to transition reversibly between expanded and contracted configurations. The slidable joint may include, for example, a tabled splice joint, a dovetail joint, a tongue and groove joint, or another suitable joint. In some embodiments, one or more mating features on the first and/or second endplates 602, 604 can include a recess (e.g., a groove, track, and/or channel), and one or more mating features on the first ramped body 606 can include a protrusion (e.g., a tongue, rail, and/or shoulder) configured to slide within the groove. In other embodiments, one or more mating features on the first and/or second endplates 602, 604 can include a protrusion and one or more mating features on the first ramped body 606 can include a recess.

As illustrated in FIG. 12A, the second end 674 of the first ramped body 606 can include a first threaded bore 688 passing longitudinally therethrough. The first threaded bore 688 may be configured to receive (e.g., threadably engage) a threaded member 704 of an actuator 702. As illustrated in FIG. 12A, the threaded member 704 of the actuator 702 can include a proximal end having a tool-engaging recess 710. As illustrated in FIGS. 12A-B, the actuator 702 can also include a washer 706 and/or a snap ring 708. The second end 674 of the first ramped body 606 can also include a second bore 690 passing longitudinally therethrough. In some embodiments, the second bore 690 may be threaded. The second bore 690 may be configured to engage an inserter. In other embodiments, the second bore 690 can advantageously be configured for use as an access port to enable graft material to be delivered into a cavity 692 (illustrated in FIG. 12C) of the device 600. The second bore 690 may be laterally displaced from the first threaded bore 688. In some embodiments, the first threaded bore 688 may be located adjacent to the second side 678 of the first ramped body 606 and the second bore 690 may be located adjacent to the first side 676, or vice versa. In other embodiments, the first threaded bore 688 may be anteriorly offset relative to the second bore 690, or vice versa. In some embodiments, illustrated in FIG. 12E, the second bore 690 can be located adjacent to the second side 678 and/or anteriorly offset relative to the first threaded bore 688. In these embodiments, the device 600 may be advantageously configured to engage an inserter at an angle offset from the plane 658, thereby enabling a user to position the device 600 in a direct lateral orientation, e.g., in a patient's lumbar spine, while reducing interaction with the psoas muscle.

The first threaded bore 688 and/or the second bore 690 can include an axis that is horizontally offset from the vertical, longitudinal plane 658. In some embodiments, the axis (e.g., of the first threaded bore 688 and/or the second bore 690) can be horizontally offset towards the second side 678. In some embodiments, the axis of the first threaded bore 688 and/or the second bore 690 can intersect the plane 658 to form an angle. In some embodiments, the angle can be in the range of from about 0° to about 90°. In other embodiments, the angle can be in the range of from about 5° to about 45°. In yet other embodiments, the angle can be in the range of from about 20° to about 30°. In still other embodiments, the angle can be equal to ε as described herein.

When in an assembled configuration, the second ramped body 608 can be disposed adjacent to the first ramped body 606. Second ramped body 608 can include one or more mating features configured to engage corresponding mating features 624, 646 on the first and/or second endplates 602, 604. The mating features on the second ramped body 608 can include some or all of the same features as the mating features 684, 686 of the first ramped body 606. As illustrated in FIG. 12A, the second ramped body 608 can include a first bore 694. The first bore 694 can be configured to be coaxial with the first threaded bore 688 of the first ramped body 606 when in an assembled configuration. The first bore 694 may be configured to receive the head portion of the actuator 702 therein. In use, the head portion may be configured to rotate within the first bore 694. The second ramped body 608 can also include a second bore 696. The first and/or second bores 694, 696 may be threaded. In some embodiments, the second bore 696 can be configured to engage an inserter. The second bore 696 can be configured to be coaxial with the second bore 690 of the first ramped body 606 when in an assembled configuration. The second bore 696 can be laterally displaced from the first bore 694. In some embodiments, the first bore 694 may be located adjacent to a second side 698 of the second ramped body 606 and the second bore 696 may be located adjacent to a first side 697, or vice versa. In other embodiments, the first bore 694 may be anteriorly offset relative to the second bore 696, or vice versa. In some embodiments, illustrated in FIG. 12E, the second bore 696 can be located adjacent to the second side 698 and/or anteriorly offset relative to the first bore 694. In these embodiments, the device 600 may be advantageously configured to engage an inserter at an angle offset from the plane 658, thereby enabling a user to position the device 600 in a direct lateral orientation, e.g., in a patient's lumbar spine, while reducing interaction with the psoas muscle.

The first bore 694 and/or the second bore 696 can include an axis that is horizontally offset from the vertical, longitudinal plane 658. In some embodiments, the axis of the first bore 694 and/or the second bore 696 can be horizontally offset towards the second side 698. In some embodiments, the axis of the first bore 694 and/or the second bore 696 can intersect the plane 658 to form an angle. In some embodiments, the angle can be in the range of from about 0° to about 90°. In other embodiments, the angle can be in the range of from about 5° to about 45°. In yet other embodiments, the angle can be in the range of from about 20° to about 30°. In still other embodiments, the angle can be equal to ε as described herein.

Figure 12D:
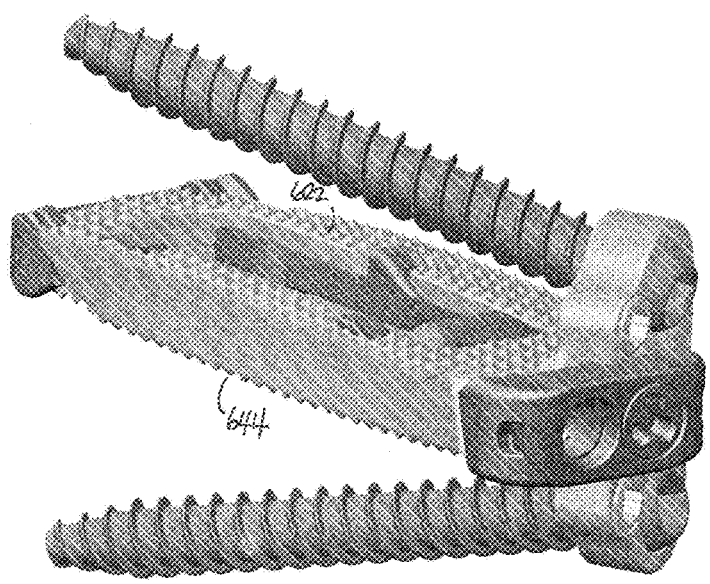
Figure 12E:
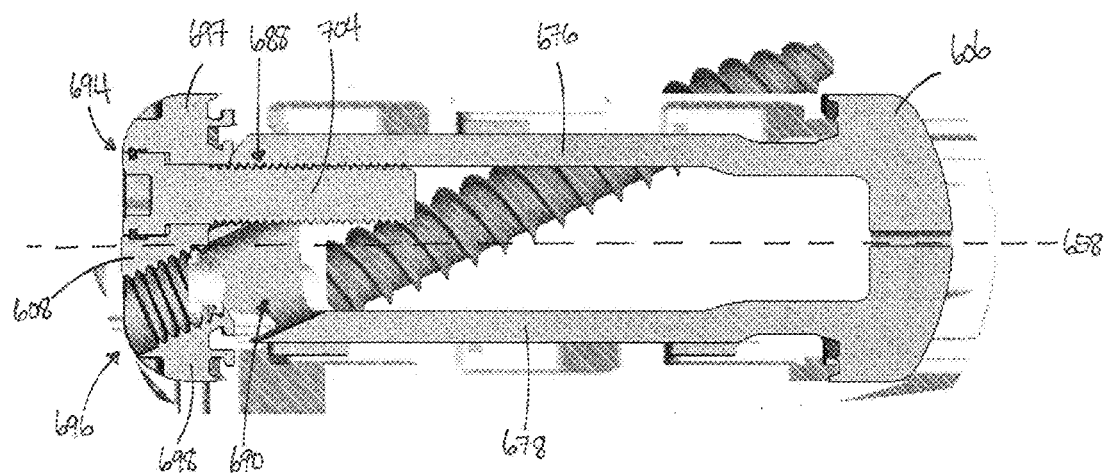
FIG. 12E illustrates a cross-sectional view of one embodiment of a vertebral fusion device described herein.
Figure 12F:
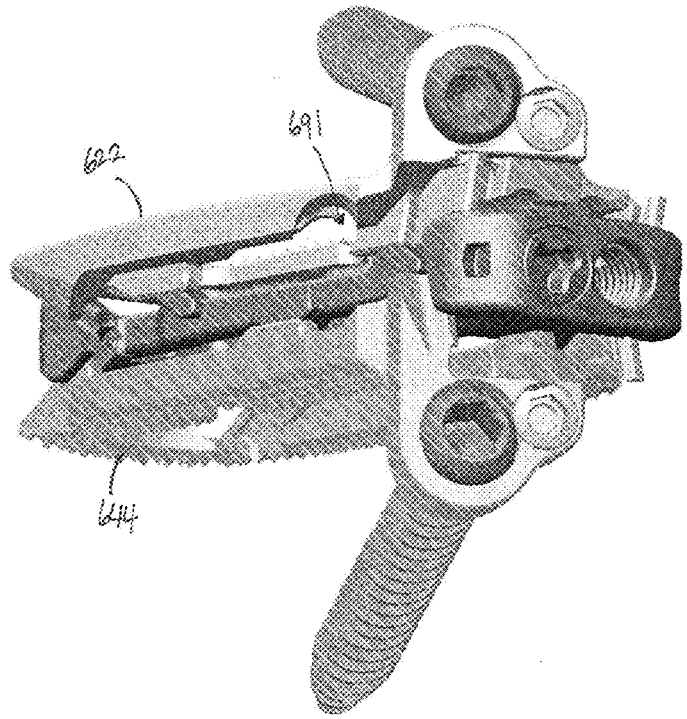
FIG. 12F illustrates a perspective view of one embodiment of a vertebral fusion device described herein.

The vertebral fusion device 600 can advantageously include an adjustable height and/or lordotic angle. In some embodiments, the device 600 may be expandable. The vertebral fusion device 600 may advantageously be configured to reversibly transition between a collapsed configuration and an expanded configuration. In the collapsed configuration, for example, as illustrated in FIG. 12D, the vertebral fusion device 600 can include a first height (e.g., as measured from the upper surface 622 of the first endplate 602 to the lower surface 644 of the second endplate 604). In the expanded configuration, for example, as illustrated in FIG. 12F, the vertebral fusion device 600 can include a second height that is greater than the first height. In some embodiments, the second height can be from about 25% to about 200% greater than the first height. In other embodiments, the second height can be from about 100% to about 150% greater than the first height. In some embodiments, the first height can be in the range of from about 5 mm to about 10 mm, and/or the second height can be in the range of from about 15 mm to about 20 mm. In some embodiments, the change in height can be caused by movement of the first and second endplates 602, 604 towards and/or away from each other. In these embodiments, the first and second endplates 602, 604 can be separated by a first distance when in the collapsed configuration and a second distance when in the expanded configuration, wherein the second distance is greater than the first distance. Those skilled in the art may appreciate that, in use, the height of the vertebral fusion device 600 can be adjusted to accommodate an individual patient's anatomy. Additionally, the device 600 may be inserted into an intervertebral space in the collapsed configuration, which may entail less trauma to surrounding tissue due to its smaller size.

Embodiments herein are also directed to methods of installing the vertebral fusion device 600. Methods can include providing the device 600 in the collapsed configuration, for example, as illustrated in FIG. 12D. In some embodiments, this step can include providing (e.g., inserting) the device 600 between two adjacent vertebrae (e.g., between the L4 and L5 vertebrae). In some embodiments, the device 600 can be inserted using an inserter, such as a straight inserter or an angled inserter. In these embodiments, the methods of installation can include coupling the inserter with the device 600, for example, threading a threaded member of the inserter into the second bore 690, 696 of the first and/or second ramps 606, 608. In some embodiments, the device 600 may be inserted along a lateral approach, for example, when a straight inserter is used. In other embodiments, the device 600 can be inserted along an anterolateral and/or oblique approach, for example, when an angled inserter is used. In these embodiments, the device 600 can be subsequently pivoted into a lateral orientation while in the intervertebral space. In some embodiments, the device 600 may be inserted using minimally invasive methods. In some embodiments, the intervertebral space may be prepared beforehand, for example, by performing a discectomy to remove some or all of the intervertebral disc.

Methods herein can also include expanding the device 600, for example, by transitioning the device 600 from the collapsed configuration to the expanded configuration. To expand the device 600, the second ramped body 608 may be moved towards the first ramped body 606, or vice versa. As the first and second ramps 606, 608 translate towards each other, the respective mating features of the first and second ramps 606, 608 may push against corresponding mating features on the first and second endplates 602, 604, thereby pushing the first and second endplates 602, 604 apart and increasing the height of the device 600.

In some embodiments, the step of expanding the device 600 can include actuating the actuator 702. This step can include applying a rotational force to the threaded member 704 to threadably engage the first ramped body 606. The rotational force can be added directly (e.g., manually) and/or indirectly (e.g., through a driver or other tool). In some embodiments, as the threaded member 704 is rotated in a first direction, the threaded member 704 may pull the first ramped body 606 towards the second ramped body 608. As the first ramped body 606 moves towards the second ramped body 608, the mating features on the first ramped body 606 may engage the mating features on the first and/or second endplates 602, 604, thereby pushing (e.g., wedging) the first and second endplates 602, 604 apart. In other embodiments, as the threaded member 704 is rotated in a second direction, the threaded member 704 may push the first ramped body 606 away from the second ramped body 608. Those skilled in the art may appreciate that the device 600 may be reversibly expandable. Accordingly, some embodiments can include reducing the height of the device 600, for example, by bringing the first and second endplates 602, 604 together.

In some embodiments, the device 600 can include a locking member configured to lock the device 600 in a desired configuration (e.g., at a desired height). In other embodiments, after the device 600 is expanded, bone growth material may be introduced into the cavity 692 through a channel 691, as illustrated in FIG. 12F. The channel 691 may pass through the first and/or second endplates 602, 604 from the outer surface 614, 638 to the cavity 692. In some embodiments, the channel 691 may be located on the second side 620, 636 of the first and/or second endplates 602, 604. Advantageously, the channel 691 may be positioned at a location (e.g., on the second side 620 and/or 636) configured to enable direct access by a surgeon in situ. In embodiments that include movable extension portions 648, 660, methods herein can also include the step of adjusting a position of one or both extension portions 648, 660 relative to at least one of the body portions of the first and second endplates 602, 604. In some embodiments, this step may be accomplished by translating (e.g., sliding) one or both extension portions 648, 660 along the respective body portions of the first and second endplates 602, 604. For example, this step can include sliding a tongue member of at least one of the first and second extension portions 648, 660 within a groove member of at least one of the respective body portions of the first and/or second endplates 602, 604. In other embodiments, the first and/or second extension portions 648, 660 may be pivoted and/or articulated relative to the respective body portions of the first and/or second endplates 602, 604. Some embodiments can also include locking the position of at least one of the first and second extension portions 648, 660 relative to the respective body portions of the first and/or second endplates 602, 604.

Methods herein can also include the step of inserting fastener 651 into bore 650 and/or inserting fastener 663 into bore 662. This step can include inserting fastener 651 along an axis (e.g., axis 652) that is configured to intersect the longitudinal axis 626 and/or the vertical, longitudinal plane 658. This step can also include inserting fastener 663 along an axis (e.g., axis 668) that is configured to intersect the longitudinal axis 670 and/or the vertical, longitudinal plane 658. In some embodiments, this step can include inserting fastener 651 and/or fastener 663 along an anterolateral and/or oblique trajectory. In other embodiments, this step can include inserting fastener 651 into a superior vertebra and inserting fastener 663 into an inferior vertebra. As described herein, those skilled in the art may appreciate that this trajectory may advantageously avoid certain anatomical structures, such as the psoas major, lumbar plexus, and/or iliac crest. Accordingly, in some embodiments, device 600 may be inserted laterally between lumbar vertebrae and subsequently coupled to the vertebrae with minimal interference. After the fasteners 651 and/or 663 have been inserted, they may be secured by retention member 656 and/or 666. The retention members 656, 666 may be disposed within the receptacles 654, 664. The retention members 656, 666 may be configured to rotate until a portion of the retention members 656, 666 overlaps the bore 650, 662 and prevents the fasteners 651, 663 from backing out. Those skilled in the art may appreciate that in some embodiments, the fasteners 651, 663 may be inserted prior to expansion of the device 600.

Figure 13A:
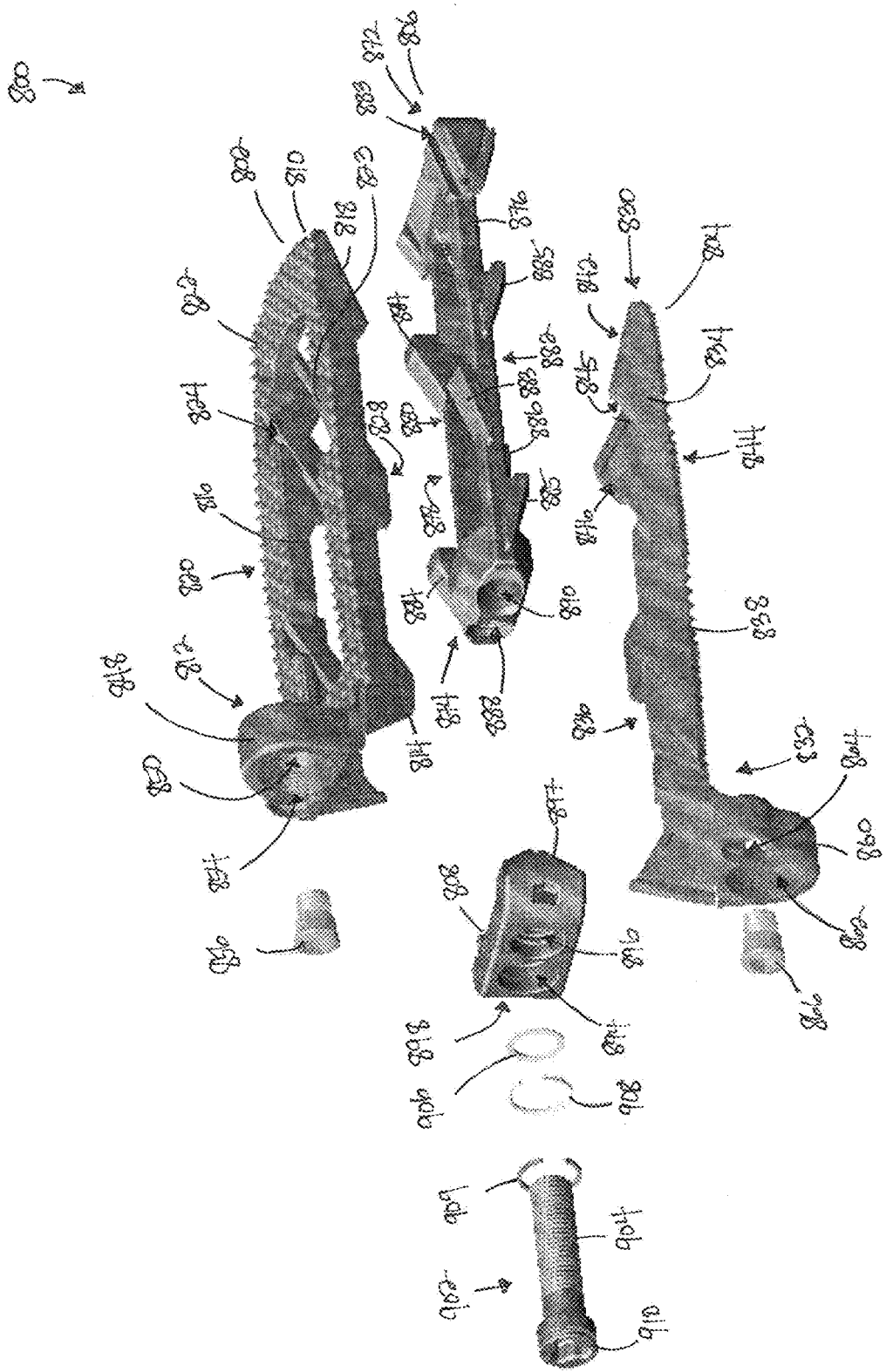
FIG. 13A illustrates an exploded view of one embodiment of a vertebral fusion device described herein.

Turning now to FIGS. 13A-E, an alternative embodiment of a vertebral fusion device is illustrated. Unless otherwise described herein, vertebral fusion device 800 can include some or all of the features of the vertebral fusion devices described in U.S. patent application Ser. No. 14/449,428, entitled "VARIABLE LORDOSIS SPACER AND RELATED METHODS OF USE," filed Aug. 1, 2014, U.S. Patent Publication No. 2014/0163683, entitled "EXPAND- ABLE VERTEBRAL IMPLANT," published Jun. 12, 2014, and U.S. Patent Publication No. 2013/0023993, entitled "EXPANDABLE FUSION DEVICE AND METHOD OF INSTALLATION THEREOF," published Jan. 23, 2013. Vertebral fusion device 800 can include a first (e.g., upper and/or superior) endplate 802, a second (e.g., lower and/or inferior) endplate 804, a first engagement, angled or ramped body 806, and a second engagement, angled surface or ramped body 808. As illustrated in FIG. 13D, the device 800 can also include a first side 801 and a second side 803. As described further herein, vertebral fusion device 800 can include an adjustable height and/or lordotic angle. In some embodiments, one or both of the first and second sides 801, 803 may be configured to pivotably expand about a pivot point P. The vertebral fusion device 800 may be wedge-shaped along a latitudinal axis, such as seen from the front view shown in FIG. 13D. For example, the device 800 may have a height that increases from the first side 801 to the second side 803. In some embodiments, the first and/or second ramped bodies 806, 808 may be wedge-shaped.

As illustrated in FIG. 13A, first endplate 802 can include a body portion that can include a first (e.g., leading and/or distal) end 810, a second (e.g., trailing and/or proximal) end 812, a first (e.g., posterior) side 818, and a second (e.g., anterior) side 820. The first endplate 802 can extend from the first side 801 to the second side 803 of the device 800. The body portion of the first endplate 802 can also include an outer surface 814, an inner surface 816, an upper surface 822, and a lower surface 828. The upper surface 822 can include a plurality of protrusions (e.g., bumps, teeth, and/or peaks) configured to engage a vertebral body. The upper surface 822 can be generally planar, concave, and/or convex. As described further herein, the first endplate 802 can include one or more mating features. In some embodiments, the mating feature(s) may be located on the inner surface 816. The first side 818 may include at least one mating feature 823, and the second side 820 may include at least one mating feature 824. In yet other embodiments, the first and/or second sides 818, 820 can each include a mating feature at the first end 810, a mating feature at an intermediate portion, and/or a mating feature at the second end 812.

As illustrated in FIG. 13A, the first endplate 802 can also include a first extension portion 848. The first extension portion 848 can extend from the second end 812 of the body portion of the first endplate 802. The first extension portion 848 can have a height that is greater than a height of the body portion of the first endplate 802. For example, the first extension portion 848 may extend beyond the upper surface 822. In some embodiments, the first extension portion 848 may be coupled (e.g., attached, joined, and/or connected) to the body portion of the first endplate 802. In some embodiments, the first extension portion 848 may be moveably (e.g., articulably and/or jointedly) coupled to the body portion of the first endplate 802, for example, as described herein with respect to vertebral fusion device 50. For example, the body portion of the first endplate 802 and the extension portion 848 may together form a dovetail joint. In some embodiments, the first extension portion 848 and the body portion of the first endplate 802 may each include a different material (e.g., a metal and/or a polymer). In other embodiments, the first extension portion 848 and the body portion of the first endplate 802 may form a unitary body. The first extension portion 848 can include a bore 850 passing therethrough. The bore 850 can be configured to receive a fastener therein. The first extension portion 848 can also include a receptacle 854. The receptacle 854 may at least partially overlap the bore 850. The receptacle 854 may be configured to receive a retention member 856 therein.

Figure 13B:
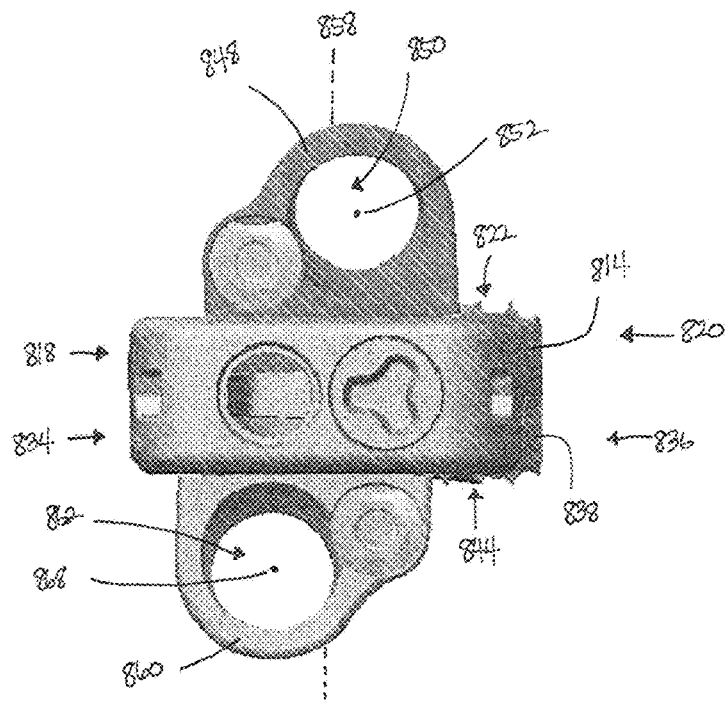

As illustrated in FIG. 13B, the bore 850 can include an axis 852. In some embodiments, axis 852 may be generally parallel to a longitudinal axis (e.g., midline) and/or a vertical, longitudinal plane 858 of the assembled device 800. In other embodiments, axis 852 may be skewed relative to the vertical, longitudinal plane 858. In yet other embodiments, axis 852 may be configured to intersect the vertical, longitudinal plane 858. In some embodiments, the axis 852, bore 850, and/or first extension portion 848 may be horizontally offset from the longitudinal midline and/or vertical, longitudinal plane 858. In some embodiments, the axis 852, bore 850, and/or first extension portion 848 may be horizontally offset towards the second side 820. In other embodiments, the axis 852, bore 850, and/or first extension portion 848 may be horizontally offset towards the first side 818. In some embodiments, the axis 852 can intersect the plane 858 by an angle in the range of from about 0° to about 90°. In other embodiments, the axis 852 can intersect the plane 858 by an angle in the range of from about 5° to about 45°. In yet other embodiments, the axis 852 can intersect the plane 858 by an angle in the range of from about 20° to about 30°.

Second endplate 804 can include some or all of the same features as the first endplate 802. In some embodiments, the first and second endplates 802, 804 may be symmetrical with respect to each other. As illustrated in FIG. 12A, second endplate 804 can include a body portion that can include a first (e.g., leading and/or distal) end 830, a second (e.g., trailing and/or proximal) end 832, a first (e.g., posterior) side 834, and a second (e.g., anterior) side 836. The second endplate 804 can extend from the first side 801 to the second side 803 of the device 800. As illustrated in FIG. 13A, the body portion of the second endplate 804 can also include an outer surface 838, an inner surface 840 (illustrated in FIG. 13D), an upper surface 842, and a lower surface 844. The lower surface 844 can include a plurality of protrusions (e.g., bumps, teeth, and/or peaks) configured to engage a vertebral body. The lower surface 844 can be generally planar, concave, and/or convex. As described further herein, the second endplate 804 can include one or more mating features. In some embodiments, the mating feature(s) may be located on the inner surface 840. The first side 834 may include at least one mating feature 845, and the second side 820 may include at least one mating feature 846. In yet other embodiments, the first and/or second sides 834, 836 can each include a mating feature at the first end 830, a mating feature at an intermediate portion, and/or a mating feature at the second end 832.

As illustrated in FIG. 13A, the second endplate 804 can also include a second extension portion 860. The second extension portion 860 can extend from the second end 832 of the body portion of the second endplate 804. The second extension portion 860 can have a height that is greater than a height of the body portion of the second endplate 804. For example, the second extension portion 860 may extend beyond the lower surface 844. In some embodiments, the second extension portion 860 may be coupled (e.g., attached, joined, and/or connected) to the body portion of the second endplate 804. In some embodiments, the second extension portion 860 may be articulably and/or jointedly coupled to the body portion of the second endplate 804, for example, as described herein with respect to vertebral fusion device 50. For example, the body portion of the second endplate 804 and the second extension portion 860 may together form a dovetail joint. In some embodiments, the second extension portion 860 and the body portion of the second endplate 804 may each include a different material (e.g., a metal and/or a polymer). In other embodiments, the second extension portion 860 and the body portion of the second endplate 804 may form a unitary body. The second extension portion 860 can include a bore 862 passing therethrough. The bore 862 can be configured to receive a fastener therein. The second extension portion 860 can also include a receptacle 864. The receptacle 864 may at least partially overlap the bore 862. The receptacle 864 may be configured to receive a retention member 866 therein.

As illustrated in FIG. 13B, the bore 862 can include an axis 868. In some embodiments, axis 868 may be generally parallel to a longitudinal axis (e.g., midline) and/or the vertical, longitudinal plane 858. In other embodiments, axis 868 may be skewed relative to the vertical, longitudinal plane 858. In yet other embodiments, axis 868 may be configured to intersect the vertical, longitudinal plane 858. In some embodiments, the axis 868, bore 862, and/or second extension portion 860 may be horizontally offset from the longitudinal midline and/or vertical, longitudinal plane 858. In some embodiments, the axis 868, bore 862, and/or second extension portion 860 may be horizontally offset towards the second side 836. In other embodiments, the axis 868, bore 862, and/or second extension portion 860 may be horizontally offset towards the first side 834. In some embodiments, the axis 868 can intersect the plane 858 by an angle in the range of from about 0° to about 90°. In other embodiments, the axis 868 can intersect the plane 858 by an angle in the range of from about 5° to about 45°. In yet other embodiments, the axis 868 can intersect the plane 858 by an angle in the range of from about 20° to about 30°.

Mating feature 823 may be generally similar to mating feature 824, except that mating feature 824 may have different (e.g., larger) dimensions than mating feature 823. In some embodiments, mating features 823, 824 of the first endplate 802 may be inclined (e.g., may extend from lower surface 828 towards upper surface 822) along longitudinal axis 826 (illustrated in FIG. 13C) in a direction from the second end 812 towards the first end 810. In some embodiments, mating features 823, 824 may be angled, e.g., towards the first end 810. In other embodiments, mating features 823, 824 may be inclined along the longitudinal axis 826 in a direction from the first end 810 towards the second end 812. Mating feature 845 may be generally similar to mating feature 846, except that mating feature 846 may have different (e.g., larger) dimensions than mating feature 845. In some embodiments, mating features 845, 846 of the second endplate 804 may be declined (e.g., may extend from upper surface 842 towards lower surface 844) along longitudinal axis 826 in a direction from the second end 832 towards the first end 830. In some embodiments, mating features 845, 846 may be angled, e.g., towards the first end 830. In other embodiments, mating features 845, 846 may be declined along the longitudinal axis 826 from the first end 830 towards the second end 832. Those skilled in the art may appreciate that mating features 823, 824 of the first endplate 802 may be symmetrical to (e.g., mirror images of) mating features 845, 846 of the second endplate 804.

As described further herein, the first and/or second endplates 802, 804 may be configured to engage (e.g., mate with) the first ramped body 806. As illustrated in FIG. 13A, the first ramped body 806 can include a first (e.g., leading and/or distal) end 872, a second (e.g., trailing and/or proximal) end 874, a first (e.g., posterior) side portion 876, and a second (e.g., anterior) side portion 878. The first ramped body 806 can also include a third (e.g., superior) end 880 and a fourth (e.g., inferior) end 882. The first ramped body 806 may extend from the first side 801 to the second side 803 of the device 800. The first ramped body 806 can include a plurality of mating features configured to engage the mating features on the first and/or second endplates 802, 804. As illustrated in FIGS. 13A and 13E, the third end 880 can include one or more mating features 883 on the first side 876 and one or more mating features 884 on the second side 878. The fourth end 882 can include one or more mating features 885 on the first side 876 and one or more mating features 886 on the second side 878. Those skilled in the art may appreciate that mating features 884, 886 may extend in generally opposite vertical directions. Additionally, mating features 883, 885 may extend in generally opposite vertical directions. In some embodiments, the first side portion 876 can include at least two mating elements 883 and at least two mating elements 885. In other embodiments, the second side portion 878 can include at least two mating elements 884 and at least two mating elements 886. In some embodiments, the first end 872 of the first ramped body 806 can include mating features 883, 884, 885, and 886.

Each of the mating features of the first ramped body 806 may be configured (e.g., shaped) to mate with a corresponding mating feature on the first and/or second endplates 802, 804. The mating features 883, 884 may be configured to engage the mating features 823, 824 of the first endplate 802. The mating features 885, 886 may be configured to engage the mating features 845, 846 of the second endplate 804. Mating features 884, 886 may have substantially similar inclinations, when in an assembled configuration, as their corresponding mating features 824, 846. In some embodiments, each mating feature 884 is inclined towards the first end 872 of the first ramped body 806, and each mating feature 886 is declined towards the first end 872 of the first ramped body 806. In other embodiments, mating feature 884 and mating feature 886 may diverge from each other along a longitudinal axis from a position relatively adjacent to the second end 874 to a position relatively adjacent to the first end 872. In yet other embodiments, the mating features 884, 886 may be angled, e.g., towards the first end 872. In still other embodiments, one or more mating features 884 may be inclined towards the second end 874 of the first ramped body 806 and/or one or more mating features 886 may be declined towards the second end 874 of the first ramped body 806. In some embodiments, one or more mating features 884, 886 can include a protrusion (e.g., a tongue, rail, and/or shoulder). In some embodiments, the protrusion can be integrally formed with the body of the first ramped body 806, or can be a separate component. For example, in some embodiments, a series of external pins can create a protrusion in the form of a rail. In other embodiments, one or more mating features 884, 886 can include a recess (e.g., a groove, track, and/or channel). In some embodiments, for example, as illustrated in FIGS. 13A and 13E, the mating features 884, 886 can alternate longitudinally along the second side 878. Each mating feature 884 on the first ramped body 806 can be generally the same. Each mating feature 886 may be generally the same. In some embodiments, at least one mating feature 884 and/or 886 may include different properties as compared to the other mating features 884, 886. Mating feature(s) 883 may be similar to mating feature(s) 884, except that mating feature(s) 884 may have different (e.g., larger) dimensions than mating feature(s) 883. Mating feature(s) 885 may be similar to mating feature(s) 886, except that mating feature(s) 886 may have different (e.g., larger) dimensions than mating feature(s) 885. In some embodiments, the mating features 883, 885 can alternate longitudinally along the first side 876. In other embodiments, the mating features 883, 884 can alternate transversely along the third end 880 of the first and/or second sides 876, 878. In yet other embodiments, the mating features 885, 886 can alternate transversely along the fourth end 882 of the first and/or second sides 876, 878. In some embodiments, each mating feature 883 may be generally the same. In other embodiments, each mating feature 885 may be generally the same. In yet other embodiments, at least one of the mating features 883, 885 may include different properties as compared to the other mating features 883, 885.

The mating features 823, 824 on the first endplate 802 may be configured to form a slidable joint with a corresponding mating feature 883, 884 on the first ramped body 806. The mating features 845, 846 on the second endplate 804 may be configured to form a slidable joint with a corresponding mating feature 885, 886 on the first ramped body 806. Accordingly, the first ramped body 806 may be configured to slideably engage the first and/or second endplates 802, 804. The slideable joint may advantageously enable the vertebral fusion device 800 to transition reversibly between expanded and contracted configurations. The slidable joint may include, for example, a tabled splice joint, a dovetail joint, a tongue and groove joint, or another suitable joint. In some embodiments, one or more mating features on the first and/or second endplates 802, 804 can include a recess (e.g., a groove, track, and/or channel), and one or more mating features on the first ramped body 806 can include a protrusion (e.g., a tongue, rail, and/or shoulder) configured to slide within the groove. In other embodiments, one or more mating features on the first and/or second endplates 802, 804 can include a protrusion and one or more mating features on the first ramped body 806 can include a recess.

The mating features 883, 884, 885, 886 on the first ramped body 806 may be curved in order to impart curvature to the first and second sides 801, 803 of the device 800. Advantageously, one or more of the curvatures of the mating features 883, 884, 885, 886 can be in the form of a helix, which results in the first endplate 802 and the second endplate 804 moving not just parallel away from one another, but also at an angle (as shown in FIG. 13D). The mating features of the first ramped body 806 may have a radius of curvature about the pivot point P. Furthermore, as the mating features of the first ramped body 806 may be complementary to corresponding mating features on the first and second endplates 802, 804, the mating features on the first and/or second endplates 802, 804 may also be curved (e.g., may include a radius of curvature about the pivot point P).

As illustrated in FIG. 13A, the second end 874 of the first ramped body 806 can include a first threaded bore 888 passing longitudinally therethrough. The first threaded bore 888 may be configured to receive (e.g., threadably engage) a threaded member 904 of an actuator 902. As illustrated in FIG. 13A, the threaded member 904 of the actuator 902 can include a proximal end having a tool-engaging recess 910. The actuator 902 can also include a washer 906 and/or one or more snap rings 908, 909. The second end 874 of the first ramped body 806 can also include a second bore 890 passing longitudinally therethrough. In some embodiments, the second bore 890 may be threaded. The second bore 890 may be configured to engage an inserter. In other embodiments, the second bore 890 can advantageously be configured for use as an access port to enable bone growth material to be delivered into a cavity of the device 800. The second bore 890 may be laterally displaced from the first threaded bore 888. In some embodiments, the first threaded bore 888 may be located adjacent to the second side 878 of the first ramped body 806 and the second bore 890 may be located adjacent to the first side 876, or vice versa. In other embodiments, the first threaded bore 888 may be anteriorly offset relative to the second bore 890, or vice versa. In some embodiments, the second bore 890 can be located adjacent to the second side 878 and/or anteriorly offset relative to the first threaded bore 888. In these embodiments, the device 800 may be advantageously configured to engage an inserter at an angle offset from the plane 858, thereby enabling a user to position the device 800 in a direct lateral orientation, e.g., in a patient's lumbar spine, while reducing interaction with the psoas muscle.

The first threaded bore 888 and/or the second bore 890 can include an axis that is horizontally offset from the vertical, longitudinal plane 858. In some embodiments, the axis (e.g., of the first threaded bore 888 and/or the second bore 890) can be horizontally offset towards the second side 878. In some embodiments, the axis (e.g., of the first threaded bore 888 and/or the second bore 890) can be parallel or skewed relative to the vertical, longitudinal plane 858. In other embodiments, the axis of the first threaded bore 888 and/or the second bore 890 can intersect the plane 858 to form an angle. In some embodiments, the angle can be in the range of from about 0° to about 90°. In other embodiments, the angle can be in the range of from about 5° to about 45°. In yet other embodiments, the angle can be in the range of from about 20° to about 30°.

When in an assembled configuration, the second ramped body 808 can be disposed adjacent to the first ramped body 806. The second ramped body 808 can extend from the first side 801 to the second side 803 of the device 800. Second ramped body 808 can include one or more mating features configured to engage corresponding mating features 823, 824, 845, 846 on the first and/or second endplates 802, 804. The mating features on the second ramped body 808 can include some or all of the same features as the mating features 883, 884, 885, 886 of the first ramped body 806. For example, the mating features on the second ramped body 808 can be curved in order to impart curvature to the first and second sides 801, 803 of the device 800. As illustrated in FIG. 13A, the second ramped body 808 can include a first bore 894. The first bore 894 can be configured to be coaxial with the first threaded bore 888 of the first ramped body 806 when in an assembled configuration. The first bore 894 may be configured to receive the head portion of the actuator 902 therein. In use, the head portion may be configured to rotate within the first bore 894. The second ramped body 808 can also include a second bore 896. The first and/or second bores 894, 896 may be threaded. In some embodiments, the second bore 896 can be configured to engage an inserter. The second bore 896 can be configured to be coaxial with the second bore 890 of the first ramped body 806 when in an assembled configuration. The second bore 896 can be laterally displaced from the first bore 894. In some embodiments, the first bore 894 may be located adjacent to a second side 898 of the second ramped body 808 and the second bore 896 may be located adjacent to a first side 897, as illustrated in FIG. 13A. In other embodiments, the first bore 894 may be located adjacent to the first side 897 and the second bore 896 may be located adjacent to the second side 898. In other embodiments, the first bore 894 may be anteriorly offset relative to the second bore 896, or vice versa. In some embodiments, the second bore 896 can be located adjacent to the second side 898 and/or anteriorly offset relative to the first bore 894. In these embodiments, the device 800 may be advantageously configured to engage an inserter at an angle offset from the plane 858, thereby enabling a user to position the device 800 in a direct lateral orientation, e.g., in a patient's lumbar spine, while reducing interaction with the psoas muscle.

The first threaded bore 894 and/or the second bore 896 can include an axis that is horizontally offset from the vertical, longitudinal plane 858. In some embodiments, the axis of the first bore 894 and/or the second bore 896 can be horizontally offset towards the second side 898. In some embodiments, the axis of the first bore 894 and/or the second bore 896 can be parallel and/or skewed relative to the plane 858. In other embodiments, the axis of the first bore 894 and/or the second bore 896 can intersect the plane 858 to form an angle. In some embodiments, the angle can be in the range of from about 0° to about 90°. In other embodiments, the angle can be in the range of from about 0° to about 45°. In yet other embodiments, the angle can be in the range of from about 20° to about 30°.

Figure 13C:
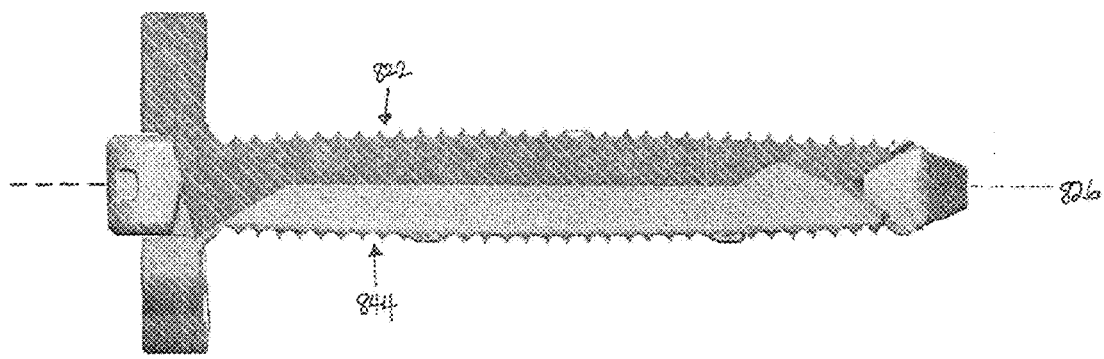

The vertebral fusion device 800 can advantageously include an adjustable height and/or lordotic angle. In some embodiments, the device 800 may be expandable. The vertebral fusion device 800 may advantageously be configured to reversibly transition between a collapsed configuration and an expanded configuration. In the collapsed configuration, for example, as illustrated in FIGS. 13B-C, the vertebral fusion device 800 can include a first height (e.g., as measured from the upper surface 822 of the first endplate 802 to the lower surface 844 of the second endplate 804). In some embodiments, the device 800 (e.g., first and second endplates 802, 804) may define a first angle when in the collapsed configuration. In other embodiments, the first and second endplates 802, 804 may be generally parallel when in the collapsed configuration. In some embodiments, the first endplate 802 and the second endplate 804 can begin at an angle, and can be expanded to a greater angle.

In the expanded configuration, for example, as illustrated in FIGS. 13D-E, the vertebral fusion device 800 can include a second height that is greater than the first height. In some embodiments, the second height can be from about 25% to about 200% greater than the first height. In other embodiments, the second height can be from about 100% to about 150% greater than the first height. In some embodiments, the first height can be in the range of from about 5 mm to about 10 mm, and/or the second height can be in the range of from about 15 mm to about 20 mm. In some embodiments, the change in height can be caused by movement of the first and second endplates 802, 804 towards and/or away from each other. In these embodiments, the first and second endplates 802, 804 can be separated by a first distance when in the collapsed configuration and a second distance when in the expanded configuration, wherein the second distance is greater than the first distance. Those skilled in the art may appreciate that, in use, the height of the vertebral fusion device 800 can be adjusted to accommodate an individual patient's anatomy. Additionally, the device 800 may be inserted into an intervertebral space in the collapsed configuration, which may entail less trauma to surrounding tissue due to its smaller size.

In other embodiments, at least one of the first and second endplates 802, 804 may be configured to pivot about pivot point P, illustrated in FIG. 13D. In these embodiments, the change in height can be caused by pivoting the first and/or second endplates 802, 804 about pivot point P. In these embodiments, the first and second endplates 802, 804 be oriented at a first angle when in the collapsed configuration. The first and/or second endplates 802, 804 can pivot apart about the pivot point P to expand the device 800 and orient the first and second endplates 802, 804 at a second angle. In some embodiments, the first (e.g., collapsed) angle can be in the range of from about 5° to about 20°. For example, the first angle may be about 10.4°. In other embodiments, the second (e.g., expanded) angle can be in the range of from about 10° to about 40°. For example, the second angle may be about 22.5°. Those skilled in the art may appreciate that in some embodiments, the device 800 can be expanded by both the linear and pivotal movement of the first and/or second endplates 802, 804 away from each other.

Embodiments herein are also directed to methods of installing the vertebral fusion device 800. Methods can include providing the device 800 in the collapsed configuration, for example, as illustrated in FIGS. 13B-C. In some embodiments, this step can include providing (e.g., inserting and/or positioning) the device 800 between two adjacent vertebrae (e.g., between the L4 and L5 vertebrae). In some embodiments, the device 800 can be inserted using an inserter, such as a straight inserter or an angled inserter. In these embodiments, the methods of installation can include coupling the inserter with the device 800, for example, threading a threaded member of the inserter into the second bore 890, 896 of the first and/or second ramped bodies 806, 808. In some embodiments, the device 800 may be inserted along a lateral approach, for example, when a straight inserter is used. In other embodiments, the device 800 can be inserted along an anterolateral and/or oblique approach, for example, when an angled inserter is used. In these embodiments, the device 800 can be subsequently pivoted into a lateral orientation while in the intervertebral space. In some embodiments, the device 800 may be inserted using minimally invasive methods. In some embodiments, the intervertebral space may be prepared beforehand, for example, by performing a discectomy to remove some or all of the intervertebral disc.

Methods herein can also include expanding the device 800, for example, by transitioning the device 800 from the collapsed configuration to the expanded configuration. This step can include pivotably expanding at least one of the first and second sides 801, 803 of the device 800. In some embodiments, the first and second sides 801, 803 may be pivotably expanded at a same angular rate of change about the pivot point P. To expand the device 800, at least one of the first and second ramped bodies 806, 808 may be translated relative to at least one of the first and second endplates 802, 804. For example, the second ramped body 808 may be moved (e.g., translated) towards the first ramped body 806, or vice versa. The mating features of the first and/or second ramped bodies 806, 808 may engage the mating features of the first and/or second endplates 802, 804. As the first and second ramped bodies 806, 808 translate towards each other, the respective mating features of the first and second ramped bodies 806, 808 may push against corresponding mating features on the first and second endplates 802, 804, thereby pushing (e.g., pivoting) the first and second endplates 802, 804 apart and increasing the height and/or angle of the device 800. The device 800 can be expanded until it defines a second angle with respect to the pivot point P, wherein the second angle is greater than the first angle.

In some embodiments, the step of expanding the device 800 can include actuating the actuator 902. This step can include inserting the threaded member 904 into the first bore 894 of the second ramped body 808 and the first threaded bore 888 of the first ramped body 806. This step can also include applying a rotational force to the threaded member 904 to threadably engage the first ramped body 806. The rotational force can be added directly (e.g., manually) and/or indirectly (e.g., through a driver or other tool). In some embodiments, as the threaded member 904 is rotated in a first direction, the threaded member 904 may pull the first ramped body 806 towards the second ramped body 808. As the first ramped body 806 moves towards the second ramped body 808, the mating features on the first ramped body 806 may engage the mating features on the first and/or second endplates 802, 804, thereby pushing (e.g., wedging and/or pivoting) the first and second endplates 802, 804 apart. In other embodiments, as the threaded member 904 is rotated in a second direction, the threaded member 904 may push the first ramped body 806 away from the second ramped body 808. Those skilled in the art may appreciate that the device 800 may be reversibly expandable. Accordingly, some embodiments can include reducing the height and/or angle of the device 800, for example, by bringing the first and second endplates 802, 804 together.

In some embodiments, the device 800 can include a locking member configured to lock the device 800 in a desired configuration (e.g., at a desired height and/or angle). In these embodiments, the methods can further include locking the device 800 in the expanded configuration. In other embodiments, after the device 800 is expanded, bone growth material may be introduced into a cavity within the device 800 through the second bores 890 and/or 896 of the first and second ramped bodies 806, 808. In some embodiments, the first and/or second endplate 802, 804 can include a channel passing from an outer surface to an inner surface and configured to receive bone graft material therethrough. In embodiments that include movable extension portions 848, 860, methods herein can also include the step of adjusting a position of one or both extension portions 848, 860 relative to at least one of the body portions of the first and second endplates 802, 804. In some embodiments, this step may be accomplished by translating (e.g., sliding) one or both extension portions 848, 860 along the respective body portions of the first and second endplates 802, 804. For example, this step can include sliding a tongue member of at least one of the first and second extension portions 848, 860 within a groove member of at least one of the respective body portions of the first and/or second endplates 802, 804. In other embodiments, the first and/or second extension portions 848, 860 may be pivoted and/or articulated relative to the respective body portions of the first and/or second endplates 802, 804. Some embodiments can also include locking the position of at least one of the first and second extension portions 848, 860 relative to the respective body portions of the first and/or second endplates 802, 804.

Methods herein can also include the step of inserting a first fastener into bore 850 along first axis 852 and/or a second fastener into bore 862 along second axis 868. In some embodiments, this step can include inserting the fastener(s) along an axis that is parallel and/or skewed relative to the vertical, longitudinal plane 858. In other embodiments, this step can include inserting the fastener(s) along an axis that is configured to intersect the vertical, longitudinal plane 858. In some embodiments, this step can include inserting the fastener(s) along an anterolateral and/or oblique trajectory. In other embodiments, this step can include inserting the first fastener into a superior vertebra and inserting the second fastener into an inferior vertebra. As described herein, those skilled in the art may appreciate that this trajectory may advantageously avoid certain anatomical structures, such as the psoas major, lumbar plexus, and/or iliac crest. Accordingly, in some embodiments, device 800 may be inserted laterally between lumbar vertebrae and subsequently coupled to the vertebrae with minimal interference. After the fasteners have been inserted, they may be secured by retention member 856 and/or 866. The retention members 856, 866 may be disposed within the receptacles 854, 864. The retention members 856, 866 may be configured to rotate until a portion of the retention members 856, 866 overlaps the bore 850, 862 and prevents the fasteners from backing out. Those skilled in the art may appreciate that in some embodiments, the first and/or second fasteners may be inserted prior to expansion of the device 800.

The devices described herein can be used in combination with various other implants and tools used in spinal surgery. In some embodiments, the implants described herein can be accompanied with other stabilizing members, including plates, rods and pedicle screws. In addition, the devices can be used with prosthetic devices or other fusion based devices.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:

1. A vertebral fusion device, comprising:
    a first endplate comprising a first extension portion, the first extension portion comprising a first bore extending therethrough;
    a second endplate comprising a second extension portion, the second extension portion comprising a second bore extending therethrough;
    a first ramp configured to mate with the first and second endplates;
    a second ramp configured to mate with the first and second endplates;
    wherein the first ramp comprises a first end and a second end, the second end comprising a first threaded bore passing longitudinally therethrough,
    wherein the second ramp comprises a first bore configured to be coaxial with the first threaded bore of the first ramp,
    wherein the first and second bores each comprise an axis wherein at least one of the axes intersects a vertical, longitudinal plane of the device; and
    wherein the vertebral fusion device comprises an adjustable height.

2. The device of claim 1, wherein the first ramp comprises at least one mating feature configured to engage a mating feature on the first endplate, and at least one mating feature configured to engage a mating feature on the second endplate.

3. The device of claim 1, wherein the first ramp is configured to slideably engage the first and second endplates.

4. The device of claim 1, wherein the second ramp comprises at least one mating feature configured to engage a mating feature on the first endplate, and at least one mating feature configured to engage a mating feature on the second endplate.

5. The device of claim 1, wherein at least one of the first and second endplates is configured to pivot about a pivot point.

6. A vertebral fusion device, comprising:
a first endplate comprising a first extension portion, the first extension portion comprising a first bore extending therethrough;
a second endplate comprising a second extension portion, the second extension portion comprising a second bore extending therethrough;
a first ramp configured to mate with the first and second endplates;
a second ramp configured to mate with the first and second endplates;
wherein the first and second bores each comprise an axis wherein at least one of the axes intersects a vertical, longitudinal plane of the device,
wherein the first ramp comprises a first end and a second end, the second end comprising a first threaded bore passing longitudinally therethrough, and
wherein the second ramp comprises a first bore configured to be coaxial with the first threaded bore of the first ramp.

7. The device of claim 6, wherein at least one of the first and second endplates is articulably coupled to at least one of the first and second extension portions.

8. The device of claim 6, wherein at least one of the first and second bores is horizontally offset from the vertical, longitudinal plane.

9. The device of claim 6, wherein at least one of the first and second extension portions is horizontally offset from the vertical, longitudinal plane.

10. The device of claim 6, wherein:
the first ramp further comprises a second bore passing longitudinally through the second end of the first ramp and laterally displaced from the first threaded bore thereof;
the second ramp further comprises a second bore laterally displaced from the first threaded bore thereof, wherein the second bore is configured to be coaxial with the second bore of the first ramp; and
the first threaded bore of the first ramp and the first bore of the second ramp each comprise an axis that intersects the vertical, longitudinal plane of the device.

11. The device of claim 10, wherein the first threaded bore of the first ramp and the first bore of the second ramp are each anteriorly offset relative to the second bore of the first ramp and the second bore of the second ramp.

* * * * *